(12) United States Patent
Snyder et al.

(10) Patent No.: US 12,017,059 B2
(45) Date of Patent: Jun. 25, 2024

(54) IMPLANTABLE HEART PUMP SYSTEMS INCLUDING AN IMPROVED APICAL CONNECTOR AND/OR GRAFT CONNECTOR

(71) Applicant: CorWave SA, Clichy (FR)

(72) Inventors: Trevor Snyder, La Celle-Saint-Cloud (FR); Amelie Bourquin, Paris (FR); Pierre-Yves Quelenn, Asnieres-sur-Seine (FR); Bastien Wittig, Epernon (FR); Tim Maher, Hamilton, MO (US); Jean Harter, Paris (FR)

(73) Assignee: CorWave SA, Clichy (FR)

( * ) Notice: Subject to any disclaimer, the term of this patent is extended or adjusted under 35 U.S.C. 154(b) by 0 days.

(21) Appl. No.: 18/509,187

(22) Filed: Nov. 14, 2023

(65) Prior Publication Data

US 2024/0157119 A1   May 16, 2024

Related U.S. Application Data

(60) Provisional application No. 63/383,886, filed on Nov. 15, 2022.

(30) Foreign Application Priority Data

Nov. 15, 2022   (EP) ..................................... 22315288

(51) Int. Cl.
*A61M 60/178*   (2021.01)
*A61M 39/12*    (2006.01)
(Continued)

(52) U.S. Cl.
CPC .......... *A61M 60/859* (2021.01); *A61M 39/12* (2013.01); *A61M 60/178* (2021.01);
(Continued)

(58) Field of Classification Search
CPC .............. A61M 60/865; A61M 60/148; A61M 60/178; A61M 31/00; A61M 1/36225;
(Continued)

(56) References Cited

U.S. PATENT DOCUMENTS 2,842,067 A   7/1958  John et al.
3,107,630 A  10/1963  Johnson et al.
(Continued)

FOREIGN PATENT DOCUMENTS

AU   2013203301 A1   5/2013
AU   2013203301 B2  10/2015
(Continued)

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).
(Continued)

*Primary Examiner* — Jon Eric C Morales
(74) *Attorney, Agent, or Firm* — Eversheds Sutherland (US) LLP; Robert D. Ward

(57) ABSTRACT

Systems and methods are provided herein for improving connections between a heart pump such a left ventricular assist device (LVAD) and the heart and/or tubing such as a graft tube. An apical connector including a cylindrical housing and a ring support connected to the housing is described. The apical connector may include a sewing ring to be connected to the patient's heart and a spring positioned within the cylindrical housing to engage a portion of the pump and secure the apical connector to the pump. Alternatively, an apical connector may include an upper and lower housing with locks positioned in channels between the housings and may include a handle and a ring to cause the locks to engage a portion of the pump. A quick connect
(Continued)

assembly is also described for efficiently connecting a graft tube to an outlet of a heart pump using a flange with through-holes and protrusions.

20 Claims, 30 Drawing Sheets

(51) Int. Cl.
    *A61M 60/148*     (2021.01)
    *A61M 60/859*     (2021.01)
    *A61M 60/865*     (2021.01)
    *A61M 39/00*     (2006.01)

(52) U.S. Cl.
    CPC . *A61M 2039/0009* (2013.01); *A61M 2205/04* (2013.01); *A61M 2210/12* (2013.01)

(58) Field of Classification Search
    CPC .. A61M 60/36; A61M 60/405; A61M 60/122; A61M 60/216; A61M 60/117; A61B 17/00234; A61B 17/0218; A61B 2017/00243; A61B 2017/1107; A61B 17/0293; A61B 2017/00252; A61B 2090/401; A61B 90/40
    See application file for complete search history.

(56) References Cited

U.S. PATENT DOCUMENTS

| | | |
|---|---|---|
| 3,165,061 A | 1/1965 | Smith et al. |
| 3,608,088 A | 9/1971 | Dorman et al. |
| 3,620,651 A | 11/1971 | Peter |
| 3,743,446 A | 7/1973 | Mandroian |
| 3,765,175 A | 10/1973 | Ohnaka |
| 4,063,826 A | 12/1977 | Riepe |
| 4,277,706 A | 7/1981 | Isaacson |
| 4,384,830 A | 5/1983 | Wakelin |
| 4,484,095 A | 11/1984 | Neumann |
| 4,488,854 A | 12/1984 | Miller |
| 4,498,851 A | 2/1985 | Kolm et al. |
| 4,648,807 A | 3/1987 | Tippetts et al. |
| 4,753,221 A | 6/1988 | Kensey et al. |
| 4,906,229 A | 3/1990 | Wampler |
| 4,918,383 A | 4/1990 | Huff et al. |
| 4,931,036 A | 6/1990 | Kanai et al. |
| 4,939,405 A | 7/1990 | Okuyama et al. |
| 4,955,856 A | 9/1990 | Phillips |
| 4,995,857 A | 2/1991 | Arnold |
| 5,147,388 A | 9/1992 | Yamazaki |
| 5,263,978 A | 11/1993 | Kaufmann et al. |
| 5,275,580 A | 1/1994 | Yamazaki |
| 5,300,111 A | 4/1994 | Panton et al. |
| 5,360,445 A | 11/1994 | Goldowsky |
| 5,370,509 A | 12/1994 | Golding et al. |
| 5,525,041 A | 6/1996 | Deak |
| 5,588,812 A | 12/1996 | Taylor et al. |
| 5,840,070 A | 11/1998 | Wampler |
| 5,924,975 A | 7/1999 | Goldowsky |
| 5,982,801 A | 11/1999 | Deak |
| 6,030,336 A | 2/2000 | Franchi |
| 6,058,593 A | 5/2000 | Siess |
| 6,079,214 A | 6/2000 | Bishop |
| 6,083,260 A | 7/2000 | Aboul-Hosn |
| 6,116,862 A | 9/2000 | Rau et al. |
| 6,123,725 A | 9/2000 | Aboul-Hosn |
| 6,176,822 B1 | 1/2001 | Nix et al. |
| 6,176,848 B1 | 1/2001 | Rau et al. |
| 6,346,071 B1 | 2/2002 | Mussivand |
| 6,361,284 B2 | 3/2002 | Drevet |
| 6,395,026 B1 | 5/2002 | Aboul-Hosn et al. |
| 6,530,876 B1 | 3/2003 | Spence |
| 6,532,964 B2 | 3/2003 | Aboul-Hosn et al. |
| 6,658,740 B2 | 12/2003 | Habben |
| 6,659,740 B2 | 12/2003 | Drevet |
| 6,672,847 B2 | 1/2004 | Dooley |
| 6,723,039 B2 | 4/2004 | French et al. |
| 6,726,648 B2 | 4/2004 | Kaplon et al. |
| 6,732,501 B2 | 5/2004 | Yu et al. |
| 6,811,381 B2 | 11/2004 | Dooley |
| 6,848,001 B1 | 1/2005 | Sakamoto et al. |
| 6,935,344 B1 | 8/2005 | Aboul-Hosn et al. |
| 6,976,996 B1 | 12/2005 | Aboul-Hosn |
| 7,011,620 B1 | 3/2006 | Siess |
| 7,027,875 B2 | 4/2006 | Siess et al. |
| 7,182,727 B2 | 2/2007 | Aboul-Hosn |
| 7,323,961 B2 | 1/2008 | Drevet |
| 7,520,850 B2 | 4/2009 | Brockway |
| 7,696,634 B2 | 4/2010 | Filardo |
| 7,736,296 B2 | 6/2010 | Siess et al. |
| 7,839,007 B2 | 11/2010 | Filardo |
| 7,863,768 B2 | 1/2011 | Filardo |
| 7,889,877 B2 | 2/2011 | Lutz |
| 7,988,728 B2 | 8/2011 | Ayre |
| 8,012,079 B2 | 9/2011 | Delgado, III |
| 8,152,845 B2 | 4/2012 | Bourque |
| 8,157,720 B2 | 4/2012 | Marseille et al. |
| 8,167,593 B2 | 5/2012 | Gohean et al. |
| 8,333,686 B2 | 12/2012 | Marseille et al. |
| 8,343,029 B2 | 1/2013 | Farnan et al. |
| 8,366,401 B2 | 2/2013 | Pate et al. |
| 8,394,009 B2 | 3/2013 | Bolyard et al. |
| 8,394,010 B2 | 3/2013 | Farnan |
| 8,432,057 B2 | 4/2013 | Filardo |
| 8,449,444 B2 | 5/2013 | Poirier |
| 8,465,410 B2 | 6/2013 | Marseille et al. |
| 8,512,012 B2 | 8/2013 | Akdis et al. |
| 8,550,975 B2 | 10/2013 | Foster |
| 8,556,795 B2 | 10/2013 | Bolyard et al. |
| 8,562,508 B2 | 10/2013 | Dague et al. |
| 8,585,571 B2 | 11/2013 | Bachman et al. |
| 8,597,350 B2 | 12/2013 | Rudser et al. |
| 8,610,304 B2 | 12/2013 | Filardo |
| 8,714,944 B2 | 5/2014 | Drevet |
| 8,753,256 B2 | 6/2014 | Bolyard et al. |
| 8,784,291 B2 | 7/2014 | Farnan et al. |
| 8,821,366 B2 | 9/2014 | Farnan et al. |
| 8,821,527 B2 | 9/2014 | Farnan et al. |
| 8,827,888 B2 | 9/2014 | Bolyard et al. |
| 8,834,136 B2 | 9/2014 | Drevet |
| 8,852,072 B2 | 10/2014 | LaRose et al. |
| 8,870,739 B2 | 10/2014 | LaRose et al. |
| 8,956,275 B2 | 2/2015 | Bolyard et al. |
| 8,976,546 B2 | 3/2015 | Wang et al. |
| 9,022,916 B2 | 5/2015 | Farnan et al. |
| 9,080,564 B2 | 7/2015 | Drevet |
| 9,089,635 B2 | 7/2015 | Reichenbach et al. |
| 9,144,669 B2 | 9/2015 | Wieselthaler |
| 9,145,875 B2 | 9/2015 | Filardo |
| 9,173,984 B2 | 11/2015 | LaRose et al. |
| 9,211,367 B2 | 12/2015 | Farnan et al. |
| 9,308,304 B2 | 4/2016 | Peters et al. |
| 9,446,180 B2 | 9/2016 | Vadala, Jr. et al. |
| 9,526,819 B2 | 12/2016 | Chen |
| 9,572,915 B2 | 2/2017 | Heuring et al. |
| 9,579,437 B2 | 2/2017 | LaRose et al. |
| 9,616,158 B2 | 4/2017 | Yaghdjian |
| 9,694,123 B2 | 7/2017 | Bourque et al. |
| 9,731,057 B2 | 8/2017 | Garrigue |
| 9,744,279 B2 | 8/2017 | Tamez et al. |
| 9,786,150 B2 | 10/2017 | Kimball et al. |
| 9,861,728 B2 | 1/2018 | Farnan et al. |
| 9,956,333 B2 | 5/2018 | LaRose et al. |
| 9,968,720 B2 | 5/2018 | Botterbusch et al. |
| 10,166,319 B2 | 1/2019 | Botterbusch et al. |
| 10,188,779 B1 | 1/2019 | Polverelli et al. |
| 10,398,821 B2 | 9/2019 | Botterbusch et al. |
| 10,799,625 B2 | 10/2020 | Scheffler et al. |
| 10,933,181 B2 | 3/2021 | Le Duc De Lillers et al. |
| 11,097,091 B2 | 8/2021 | Botterbusch et al. |
| 2001/0001278 A1 | 5/2001 | Drevet |
| 2002/0095210 A1 | 7/2002 | Finnegan et al. |
| 2002/0146333 A1 | 10/2002 | Drevet |

(56) References Cited

U.S. PATENT DOCUMENTS

| | | |
|---|---|---|
| 2002/0165426 A1 | 11/2002 | Sporer et al. |
| 2003/0002325 A1 | 1/2003 | Alvandpour et al. |
| 2004/0002624 A1 | 1/2004 | Yu et al. |
| 2005/0031474 A1 | 2/2005 | Zackl |
| 2005/0261543 A1 | 11/2005 | Abe et al. |
| 2005/0288543 A1 | 12/2005 | Stenberg et al. |
| 2006/0014999 A1 | 1/2006 | Heilman et al. |
| 2006/0155158 A1 | 7/2006 | Aboul-Hosn |
| 2006/0288543 A1 | 12/2006 | Lubera et al. |
| 2007/0299297 A1 | 12/2007 | Jarvik |
| 2008/0232987 A1 | 9/2008 | Drevet |
| 2009/0082778 A1 | 3/2009 | Beane et al. |
| 2010/0234941 A1 | 9/2010 | Finocchiaro et al. |
| 2010/0241223 A1 | 9/2010 | Lee et al. |
| 2010/0268333 A1 | 10/2010 | Gohean et al. |
| 2011/0124950 A1 | 5/2011 | Foster |
| 2011/0176945 A1 | 7/2011 | Drevet |
| 2011/0176946 A1 | 7/2011 | Drevet |
| 2011/0260449 A1 | 10/2011 | Pokorney |
| 2012/0089225 A1 | 4/2012 | Akkerman et al. |
| 2012/0177506 A1 | 7/2012 | Örter |
| 2012/0220816 A1 | 8/2012 | Peters et al. |
| 2012/0226350 A1 | 9/2012 | Rudser et al. |
| 2012/0323318 A1 | 12/2012 | Yusuf et al. |
| 2013/0042753 A1 | 2/2013 | Becker et al. |
| 2013/0078122 A1 | 3/2013 | Drevet |
| 2013/0178694 A1 | 7/2013 | Jeffery et al. |
| 2013/0267779 A1 | 10/2013 | Woolford et al. |
| 2013/0314047 A1 | 11/2013 | Eagle et al. |
| 2014/0023533 A1 | 1/2014 | Ishii et al. |
| 2014/0067057 A1 | 3/2014 | Callaway et al. |
| 2014/0187852 A1 | 7/2014 | Peters et al. |
| 2014/0207232 A1 | 7/2014 | Garrigue |
| 2014/0275723 A1 | 9/2014 | Fritz, IV et al. |
| 2014/0277423 A1 | 9/2014 | Alkhatib et al. |
| 2014/0303426 A1 | 10/2014 | Kerkhoffs et al. |
| 2014/0316426 A1 | 10/2014 | Gollner et al. |
| 2015/0167659 A1 | 6/2015 | Sauer |
| 2015/0273124 A1 | 10/2015 | Callaway et al. |
| 2015/0330383 A1 | 11/2015 | Letailleur et al. |
| 2016/0038664 A1 | 2/2016 | Callaway et al. |
| 2016/0051738 A1 | 2/2016 | Callaway et al. |
| 2016/0235899 A1 | 8/2016 | Yu et al. |
| 2016/0243294 A1 | 8/2016 | Peters et al. |
| 2017/0000934 A1 | 1/2017 | Miyakoshi |
| 2017/0012491 A1 | 1/2017 | Schob et al. |
| 2017/0266358 A1 | 9/2017 | Aber |
| 2017/0290966 A1 | 10/2017 | Botterbusch et al. |
| 2017/0290967 A1 | 10/2017 | Botterbusch et al. |
| 2017/0296723 A1 | 10/2017 | Garrigue |
| 2018/0038364 A1 | 2/2018 | Dumas et al. |
| 2018/0050143 A1 | 2/2018 | Nguyen et al. |
| 2018/0256798 A1 | 9/2018 | Botterbusch et al. |
| 2018/0369469 A1 | 12/2018 | Le Duc De Lillers et al. |
| 2019/0125949 A1 | 5/2019 | Botterbusch et al. |
| 2019/0381227 A1 | 12/2019 | Botterbusch et al. |
| 2020/0368417 A1 | 11/2020 | Polverelli et al. |
| 2021/0085845 A1 | 3/2021 | West |
| 2021/0170160 A1 | 6/2021 | Le Duc De Lillers et al. |
| 2021/0172429 A1 | 6/2021 | Drevet et al. |
| 2021/0275797 A1 | 9/2021 | Snyder et al. |
| 2021/0379353 A1 | 12/2021 | Botterbusch et al. |
| 2022/0016412 A1 | 1/2022 | Bourquin et al. |

FOREIGN PATENT DOCUMENTS

| | | |
|---|---|---|
| CA | 2712945 A1 | 7/2009 |
| CN | 1257006 A | 6/2000 |
| CN | 1355715 A | 6/2002 |
| CN | 1714759 A | 1/2006 |
| CN | 101472627 A | 7/2009 |
| CN | 101878049 A | 11/2010 |
| CN | 102112744 A | 6/2011 |
| CN | 102284092 A | 12/2011 |
| CN | 106421939 A | 2/2017 |
| CN | 106489026 A | 3/2017 |
| CN | 114367029 A | 4/2022 |
| CN | 114470512 A | 5/2022 |
| EP | 0412856 A1 | 2/1991 |
| EP | 0415949 A1 | 3/1991 |
| EP | 0412856 B1 | 1/1994 |
| EP | 0445782 B1 | 8/1994 |
| EP | 0925081 B1 | 12/2003 |
| EP | 0961621 B1 | 7/2004 |
| EP | 1551500 A2 | 7/2005 |
| EP | 1233797 B1 | 7/2006 |
| EP | 1337288 B1 | 3/2008 |
| EP | 1981585 A2 | 10/2008 |
| EP | 1644639 B1 | 2/2009 |
| EP | 2152339 A1 | 2/2010 |
| EP | 2249746 A1 | 11/2010 |
| EP | 2310067 A1 | 4/2011 |
| EP | 2600918 A1 | 6/2013 |
| EP | 2517739 B1 | 12/2013 |
| EP | 2704761 A1 | 3/2014 |
| EP | 2310067 B1 | 4/2014 |
| EP | 2753389 B1 | 7/2014 |
| EP | 2152339 B1 | 5/2015 |
| EP | 2891502 A1 | 7/2015 |
| EP | 2704761 B1 | 9/2015 |
| EP | 2736552 B1 | 9/2015 |
| EP | 2891502 B1 | 7/2016 |
| EP | 2164542 B1 | 8/2016 |
| EP | 2856190 B1 | 9/2016 |
| EP | 3141269 A1 | 3/2017 |
| EP | 3145558 A2 | 3/2017 |
| ES | 2587072 A1 | 10/2016 |
| FR | 355700 A | 11/1905 |
| FR | 2650862 B1 | 11/1991 |
| FR | 2744769 A1 | 8/1997 |
| FR | 2744769 B1 | 2/1999 |
| FR | 2861910 B1 | 1/2006 |
| FR | 2905147 A1 | 2/2008 |
| FR | 3032917 A1 | 8/2016 |
| GB | 662047 A | 11/1951 |
| JP | 2011509801 A | 3/2011 |
| KR | 20130068373 A | 6/2013 |
| WO | WO-8910763 A1 | 11/1989 |
| WO | WO-9008260 A1 | 7/1990 |
| WO | WO-9729282 A1 | 8/1997 |
| WO | WO-9959652 A1 | 11/1999 |
| WO | WO-0037126 A1 | 6/2000 |
| WO | WO-0074747 A1 | 12/2000 |
| WO | WO-2007053881 A1 | 5/2007 |
| WO | WO-2011056823 A2 | 5/2011 |
| WO | WO-2016179262 A1 | 11/2016 |
| WO | WO-2017087717 A1 | 5/2017 |
| WO | WO-2017087785 A1 | 5/2017 |
| WO | WO-2019019206 A1 | 1/2019 |
| WO | WO-2019092175 A1 | 5/2019 |
| WO | WO-2020115607 A2 | 6/2020 |

OTHER PUBLICATIONS

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Extended European Search Report dated Aug. 25, 2021 in EP Patent Application Serial No. 21168340.4 (0231).

Fatullayev, et al., Continuous-Flow Left Ventricular Assist Device Thrombosis: A Danger Foreseen is a Danger Avoided, Medical Science Monitor Basic Research, 21:141-144 (2015).

(56) References Cited

OTHER PUBLICATIONS

Feier, et al., A Novel, Valveless Ventricular Assist Device: The Fish Tail Pump. First Experimental in Vivo Studies, Artificial Organs, (26)12:1026-1031 (2002).
Fliess, et al., Flatness and Defect of Nonlinear Systems: Introductory Theory and Examples, International Journal of Control, 61(6):1327-1361 (1995).
Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).
Harris, et al., Ventricular Assist Devices, Continuing Education in Anesthesia, Critical Care & Pain, 12(3):145-151 (2012).
International Search Report & Written Opinion dated Mar. 4, 2019 in Int'l PCT Patent Appl. No. PCT/IB2018/059199, 13 pages (0510).
International Search Report & Written Opinion dated May 14, 2021 in Int'l PCT Patent Appl. Serial No. PCT/IB2021/051879 (0910).
International Search Report & Written Opinion dated Jun. 28, 2017 in Int'l PCT Patent Application Serial No. PCT/IB2017/052068 (0210).
International Search Report & Written Opinion dated Jul. 15, 2020 in Int'l PCT Patent Appl. Serial No. PCT/IB2019/060144 (0610).
International Search Report & Written Opinion dated Aug. 22, 2017 in Int'l PCT Patent Application Serial No. PCT/IB2017/052069 (0310).
International Search Report and Written Opinion dated Apr. 16, 2019 in Int'l PCT Patent Appl. Serial No. PCT/EP2018/080749 (English Translation of ISR only) (0810).
International Search Report and Written Opinion dated Jun. 25, 2020 in International PCT Patent Application Serial No. PCT/IB2020/052337 (0710 PCT).
International Search Report and Written Opinion dated Aug. 3, 2018 in Int'l PCT Patent Appl. Serial No. PCT/IB2018/052215 (0410).
Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).
Islam et al., Left Ventricular Assist Devices and Gastrointestinal Bleeding: A Narrative Review of Case Reports and Case Series, Clinical Cardiology, 36(4):190-200 (2013).
Jorde, et al., Identification and Management of Pump Thrombus in the HeartWare Left Ventricular Assist Device System, JACC: Heart Failure, 3(11):849-856 (2015).
Latham, et al., Parameter Estimation and a Series of Nonlinear Observers for the System Dynamics of a Linear Vapor Compressor, IEEE Transactions on Industrial Electronics, 63(11):6736-6744 (2016).
Leverett, et al., Red Blood Cell Damage by Shear Stress, Biophysical Journal, 12(3):257-273 (1972).
Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).
Mancini, et al., Left Ventricular Assist Devices, A Rapidly Evolving Alternative to Transplant, Journal of the American College of Cardiology, 653:2542-2555 (2015).
Mboup, et al., Numerical Differentiation With Annihilators in Noisy Environment, Numerical Algorithms, 50(4):439-467 (2009).
Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).
Mercorelli, P., A Motion-Sensorless Control for Intake Valves in Combustion Engines, IEEE Transactions on Industrial Electronics, 64(4):3402-3412 (2017).
Mercorelli, P., An Adaptive and Optimized Switching Observer for Sensorless Control of an Electromagnetic Valve Actuator in Camless Internal Combustion Engines, Asian Journal of Control, 16(4):959-973 (2014).
Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).
Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).
Pagani, Francis D., MD, PhD, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.
Perschall, et al., The Progressive Wave Pump: Numerical Multiphysics Investigation of a Novel Pump Concept With Potential to Ventricular Assist Device Application, Artificial Organs, 35(9):E179-E190 (2012).
Rahman, et al., Position Estimation in Solenoid Actuators, IEEE Transactions on Industry Applications, 32(3):552-559 (1996).
Rigatos, G., Differential Flatness Theory ad Flatness-Based Control, in Nonlinear Control and Filtering Using Differential Flatness Approaches, 25(2):47-101 (2015).
Wang, et al., Rotary Blood Pump Control Strategy for Preventing Left Ventricular Suction, ASAIO Journal, 61(1):21-30(2015).
Wang., Quadrotor Analysis and Model Free Control with Comparisons, Universite Paris Sud—Paris XI, (2013).
Weidemann, Daniel., Thesis entitled, Permanent Magnet Reluctance Actuators for Vibration Testing, Completed at the Institute of Applied Mechanics, Technische Universitat Munchen, Apr. 2013.
Yuan, et al., The Spectrum of Complications Following Left Ventricular Assist Device Placement, Journal of Cardiac Surgery, 27:630-638 (2012).
Zhang, et al., Study on Self-Sensor of Linear Moving Magnet Compressor's Piston Stroke, IEEE Sensors Journal, 9(2):154-158 (2009).
International Search Report & Written Opinion dated Oct. 9, 2023 in Int'l PCT Patent Appl. Serial No. PCT/IB2023/054203.
Invitation to Pay Additional Fees and Partial Search Report dated Feb. 7, 2024 in Int'l PCT Patent Appl. Serial No. PCT/IB2023/061509.

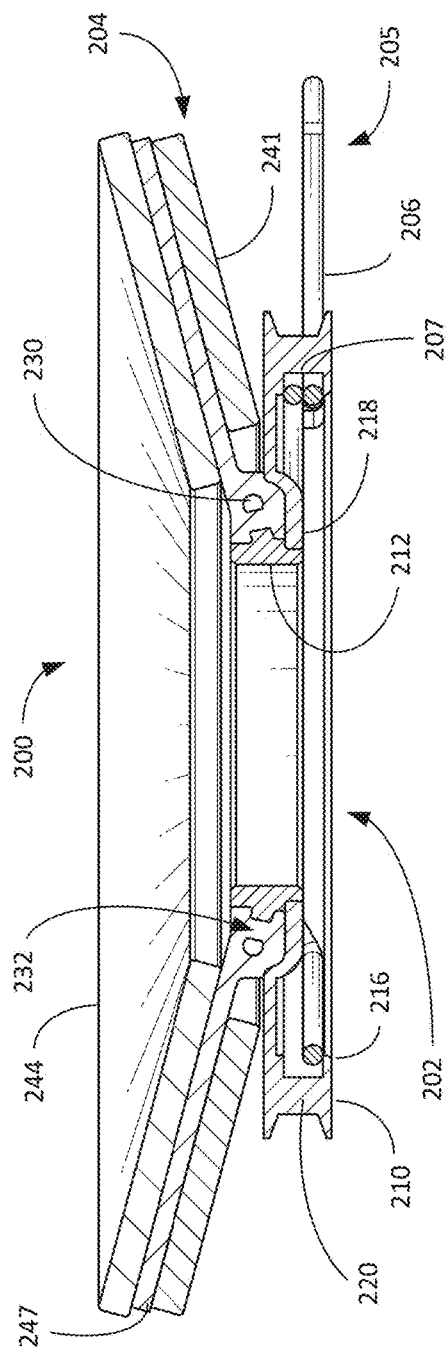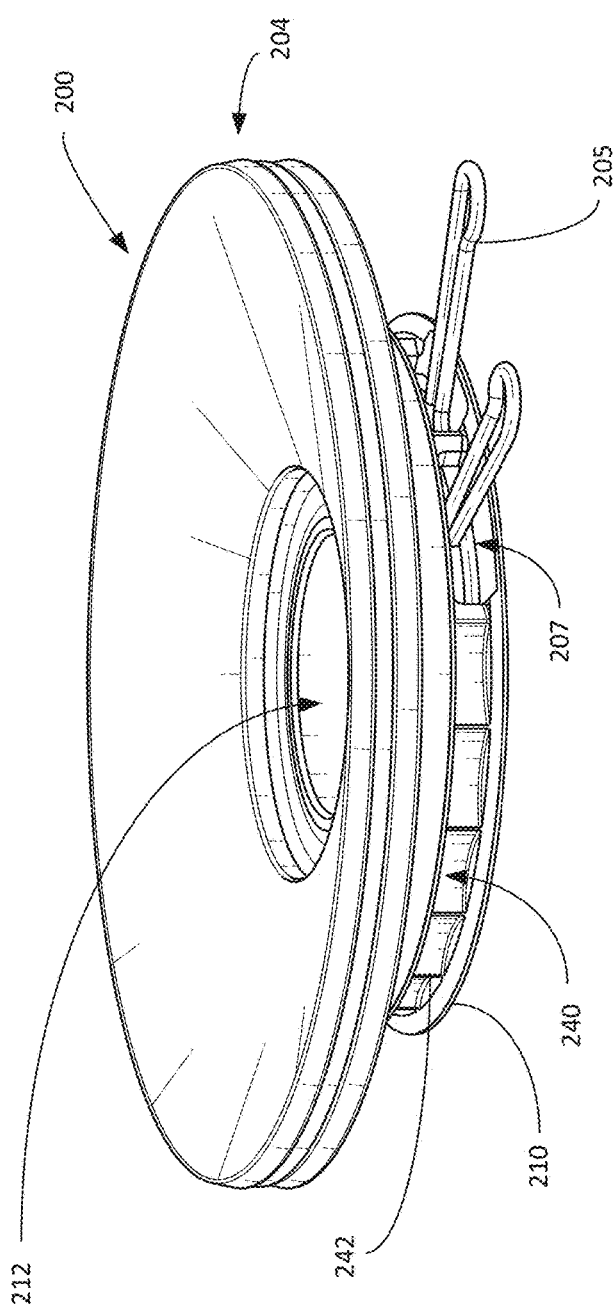

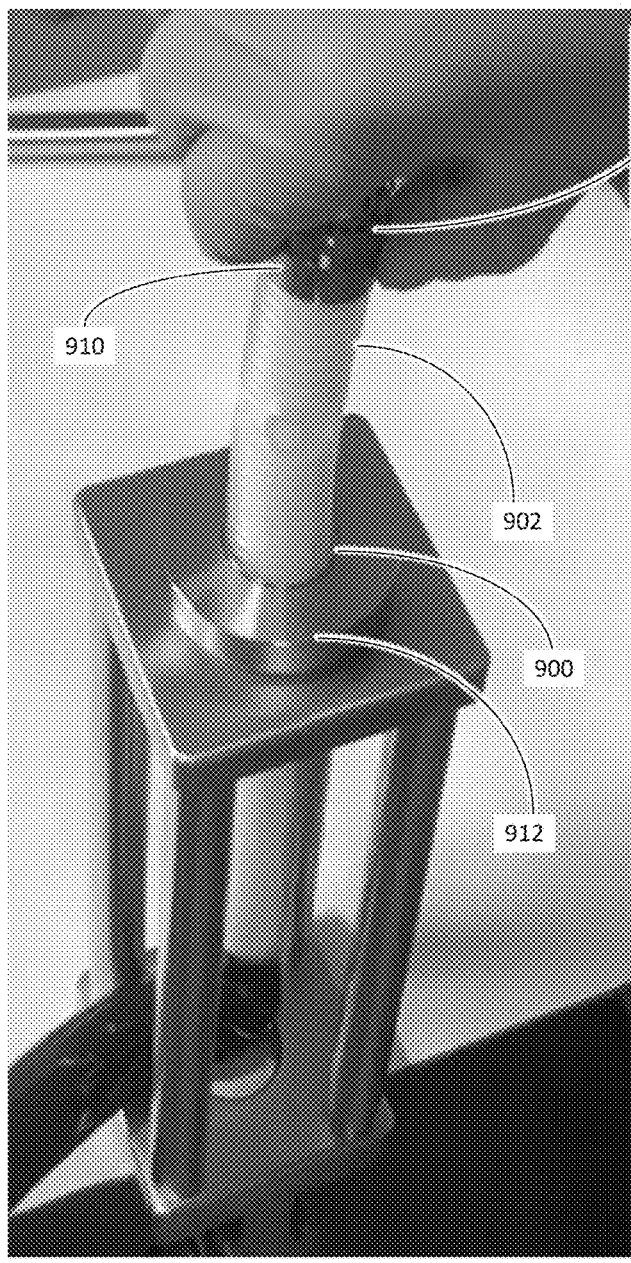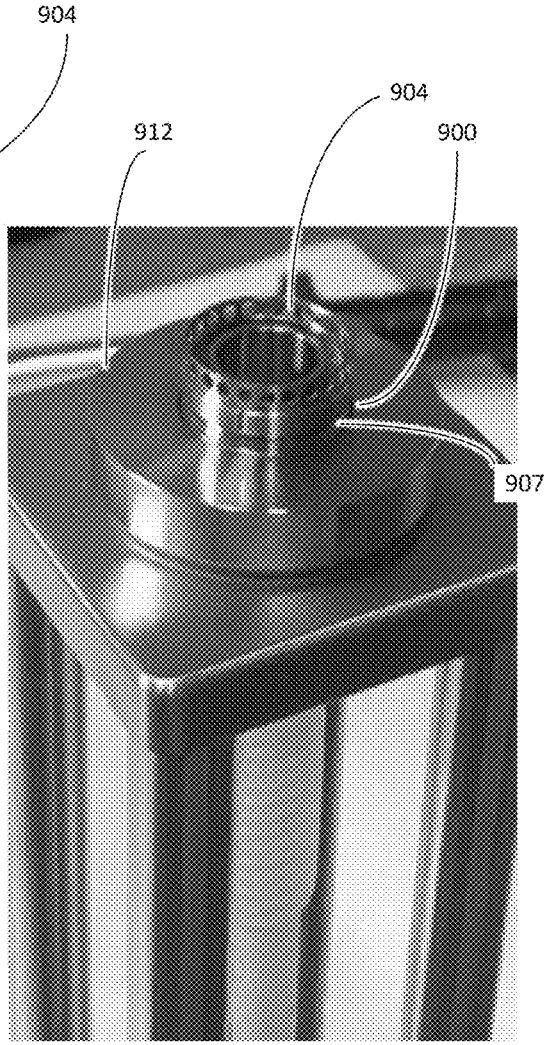
FIG. 9A
FIG. 9B

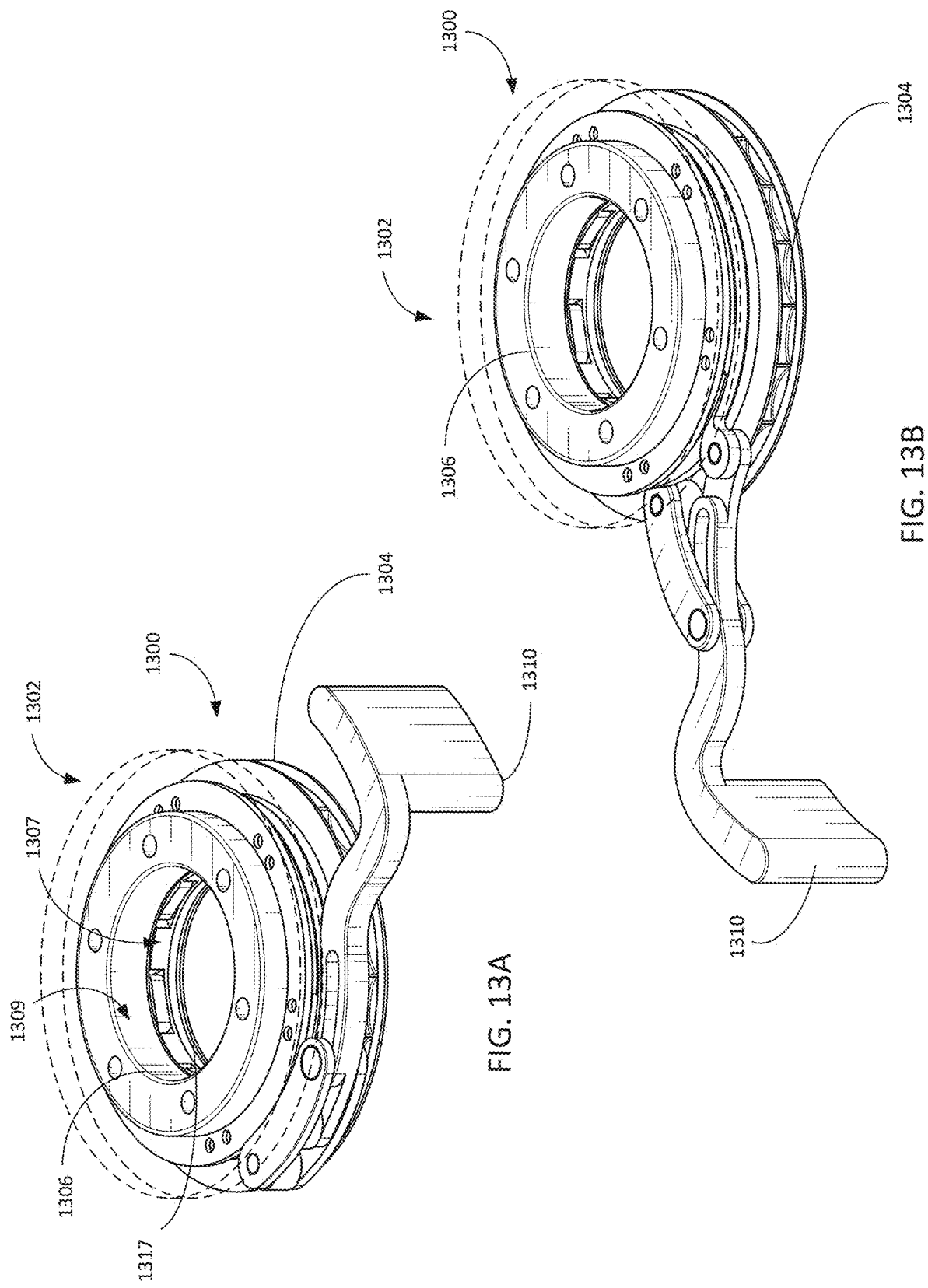

IMPLANTABLE HEART PUMP SYSTEMS INCLUDING AN IMPROVED APICAL CONNECTOR AND/OR GRAFT CONNECTOR

CROSS-REFERENCE TO RELATED APPLICATIONS

This application claims priority to U.S. Provisional Patent Application Ser. No. 63/383,886, filed Nov. 15, 2022, and European Patent Application Serial No. 22315288.5, filed Nov. 15, 2022, the entire contents of each of which are incorporated herein by reference.

TECHNICAL FIELD

The present invention relates, in general, to implantable heart pump systems and more particularly to implantable heart pump systems having an apical connector and/or a graft connector.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to pump sufficient oxygenated blood throughout the body.

For patients that have reached end stage heart failure, treatment options are limited. In addition to continued use of drug therapy commonly prescribed during earlier stages of heart failure, the typical recommendation is cardiac transplantation or implantation of a mechanical assist device. While a cardiac transplant may significantly prolong the patient's life, patients frequently expire while on a waitlist for months and sometimes years awaiting a suitable donor heart. Presently, the only alternative to a cardiac transplant is a mechanical implant. While in recent years mechanical implants have improved in design, typically such implants will prolong a patient's life by a few years at most, and include a number of co-morbidities.

One type of mechanical implant often used for patients with end stage heart failure is a left ventricular assist device (LVAD). The LVAD is a surgically implanted pump that draws oxygenated blood from the left ventricle and pumps it directly to the aorta, thereby off-loading (reducing) the pumping work of the left ventricle. LVADs typically are used either as a "bridge-to-transplant" or "destination therapy." When used for a bridge-to-transplant, the LVAD is used to prolong the life of a patient who is waiting for a heart transplant. When a patient is not suitable for a heart transplant, the LVAD may be used as a destination therapy, meaning the definitive treatment for heart failure, to prolong the life, or improve the quality of life, of the patient, but generally such prolongation is for only a couple years.

Procedures for implanting LVADs are complex and require a highly skilled surgeon. A coring tool is typically used to create a 1-2.5 cm ventriculotomy in the apex of the left ventricle and to introduce the pump inlet into the heart. The LVAD inlet cannula must be adequately secured to the heart tissue so that the inlet position is maintained within the ventricle during motion and anatomic displacements including heart contraction, breathing, and a patient bending over. Additionally, a graft must be connected from the LVAD to the patient's circulatory system (e.g, aortic arch). Grafts are often prone to twisting, folding, and/or flattening when a twist movement is applied to the graft during connection to the pump.

What is needed are further improved systems and devices for safely and efficiently securing an implantable heart pump, such as a LVAD, to a heart and for connecting graft structure to the patient's circulatory system.

SUMMARY

Provided herein are systems and methods for improving connections between an implantable heart pump such a left ventricular assist device (LVAD) and the heart and/or tubing such as a graft tube. For example, apical connectors are described including a cylindrical connector housing, ring support coupled to the housing and having an internal opening with a dimeter smaller than an internal opening the connector housing and a spring positioned within the internal opening of the housing. The ring support may further include a flange connected to a sewing ring for connecting the apical connector to a portion of a patient's heart. The spring may be positioned within the connector housing and may be designed to engage a portion of a heart pump when the heart pump is inserted into the internal opening of the housing to connect the apical connector to the patient's heart.

Yet another apical connector is described with an upper support connected to a lower support and a plurality of channels defined therebetween. The channels guide locks positioned within each channel. Each of the upper support and the lower support may have internal surfaces defining a channel extending through the apical connector. A ring may surround the locks and may cause the locks to move within the channel to partially extend past the inner surfaces. When the ring is in the closed position, the locks may engage a portion of a heart pump extending through the channel. The upper support may be connected to a sewing ring to connect the apical connector and thus the heart pump to the patient's heart.

Yet another connector is described for quickly connecting a graft tube or other tubing to an outlet or other cannula of the heart pump. The quick connect assembly may include a connector portion connected to an end of a graft tube and having a flange with holes distributed circumferentially about the connector portion and may further include a connector portion connected to an end of an outlet of the pump or other cannula having a set of protrusions for entering the holes in the flange of the connector portion connected to the graft tube. The quick connect assembly may permit a surgeon or other healthcare provider to quickly connect a graft tube to an outlet of the pump, for example.

An assembly for connecting a graft tube to a blood pump, in one example, includes a graft assembly designed to be coupled to an end of the graft tube, the graft assembly forming a cylindrical structure including an internal housing having an first outer surface and a second outer surface an external housing offset from the internal housing and defining a graft receiving area between a first inner surface of the external housing and the first outer surface of the internal housing and defining a pump receiving area between a second inner surface of external housing and the second outer surface of the internal housing, a flange extending from the cylindrical structure and having a plurality of through-holes arranged circumferentially, as well as a pump assembly designed to be coupled to a cannula of the blood pump, the pump assembly including a cylindrical protrusion sized and designed to be received in the pump receiving area, and a set of protrusions extending from the cylindrical protrusion and designed to be received by and extend through a set of through-holes of the plurality of through-holes of the flange.

The cannula may be an outlet of the blood pump and wherein the cylindrical protrusion is designed to rotatably couple to the outlet of the blood pump such that the pump assembly is free to rotate with respect to the outlet of the blood pump while the cylindrical protrusion is coupled the outlet of the blood pump. The cylindrical protrusion may include a sealing ring designed to create fluid-tight seal between the graft assembly and the pump assembly. The pump assembly may be designed to rotate with respect to the graft assembly while the cylindrical protrusion is received in the pump receiving area and the sealing ring maintains a fluid-tight seal. The pump assembly may further include a set of tabs extending from the set of protrusions, the set of tabs designed to be depressed to transition the set protrusions between an expanded position and a contracted position. The set of protrusions may be designed to move closer together when the set of tabs are in the contracted position and may be designed to move further apart when the set of tabs are in the expanded position.

The set of protrusions may be designed to lock the pump assembly to the graft assembly when the set of protrusions extend through the set of through-holes of the flange. Each protrusion of the set of protrusions may have a first end having a first height and a second end having a second height higher than the first height. Each protrusion of the set of protrusions may have a circular profile. The graft receiving area may be designed to receive and couple to the end of the graft tube to secure the graft assembly to the graft tube.

A method for connecting a graft tube to heart pump via an assembly having a graft assembly and a pump assembly, in one example, includes, positioning the graft assembly adjacent to the pump assembly, the graft assembly designed to be coupled to an end of a graft tube and having a cylindrical structure and a flange extending from the cylindrical structure and having a plurality of through-holes, the pump assembly having a cylindrical protrusion designed to be to be coupled to a cannula of the heart pump, causing a set of tabs on the pump assembly to transition to a compressed state, the set of tabs each having a protrusion and each extending from the cylindrical protrusion of the pump assembly, aligning the protrusions of each of the tabs with the through-holes of the flange of the graft assembly while the tabs are in the compressed state, causing the protrusions of each of the tabs to extend through respective through-holes of the plurality of through-holes of the flange by transitioning the set of tabs to an expanded state while the protrusions of each of the tabs are aligned with the through-holes of the flange. The cylindrical protrusion may engage and be in fluid communication with the cylindrical structure when the protrusions of each of the tabs extend through the respective through-holes.

The cylindrical structure of the graft assembly may include an internal housing and an external housing and a pump receiving area may be defined between the internal housing and the external housing. A portion of the cylindrical protrusion may be received by the pump receiving area when the protrusions of each of the tabs extend through respective through-holes of the plurality of through-holes of the flange. The cylindrical structure of the graft assembly and cylindrical protrusion of the pump assembly may form a fluid tight seal between the graft tube and the cannula when the protrusions of each of the tabs extend through respective through-holes of the plurality of through-holes of the flange.

The method may further include causing the set of tabs on the pump assembly to again transition to the compressed state, rotating the graft assembly with respect to the pump assembly while the set of tabs are in the compressed state and while maintaining the fluid tight seal between the graft tube and the cannula, and causing the protrusions of each of the tabs to extend through respective through-holes of the plurality of through-holes of the flange by again transitioning the set of tabs to the expanded state. The cylindrical protrusion may have a sealing ring and, when the cylindrical protrusion is received by the pump receiving area, the sealing ring may engage both the cylindrical protrusion and the cylindrical structure. The graft receiving area may be defined between the internal housing and the external housing and the graft receiving area may be designed to receive the end of the graft tube. The plurality of through-holes of the flange may be arranged circumferentially. Each through-hole of the plurality of through-holes may be circular in shape and the protrusions of each of the tabs may have a circular profile. The protrusions of each of the tabs are positioned closer to one another when the set of tabs are in the compressed state than when each of the tabs are in the expanded state.

An apical connector for securing a heart pump to an apex of a patient's heart, in one example, includes a housing having a first end having a first diameter and second end having a second diameter smaller than the first diameter, the first end designed to receive a portion of a the heart pump, and the second end designed to engage a cannula of the pump extending beyond the portion of the pump, a spring having an expandable portion designed to be disposed within the housing and a handle portion designed to extend through an aperture of the housing, the spring designed to transition from an expanded position to a constricted position around the protrusion of the heart pump, and a sewing ring coupled to the housing at the second end, the sewing ring designed to conform to the patient's heart and couple the apical connector to the patient's heart.

The housing may include a connector housing having the first end and a ring support having the second end, the connector housing coupled to the ring support. The connector housing may have a plurality of dimples designed to facilitate engagement with a support tool. The spring may be designed to be positioned in the connector housing and the sewing ring may be designed to be coupled to the ring support. The apical connector may further include a flange coupled at the second end to the housing and designed to be coupled to the sewing ring. The flange may include a plurality of through-holes and may be angled away from the first end. The sewing ring may include a silicon layer designed to surround at least a portion of the flange and to enter the through-holes. The sewing ring may include at least one layer of biocompatible felt and at least one layer of silicone. The sewing ring may include a first layer biocompatible felt, a second layer of silicone, and third layer of biocompatible felt, the second layer of silicone positioned between the first layer of biocompatible felt and the second layer of biocompatible felt. The spring may be designed to secure the housing to the heart pump when the spring is in the constricted position.

An apical connector for securing a heart pump to a patient's heart, the apical connector including an upper support having a first inner surface and a lower surface, a lower support having a second inner surface and an upper surface designed to engage with the lower surface of the upper support, the upper surface defining a plurality of channels, a plurality of locks each designed to move in a first direction within a respective channel of the plurality of channels toward the second inner surface and to selectively extend beyond the second inner surface, the plurality of locks constrained from movement other than in the first direction by the upper support and the lower support, a lock assembly including a ring and a handle designed to transition the ring from an open position to a closed position, wherein the closed position of the ring causes the plurality of locks to move in the first direction to partially extend beyond the second inner surface.

The apical connector may further include a sewing ring coupled the upper support, the sewing ring designed to conform to the patient's heart and couple the apical connector to the patient's heart. The sewing ring may be designed to be coupled to the patient's heart via one or more suture. The sewing ring may include silicone inserted between layers of biocompatible felt. The ring may be designed to push the plurality of locks through respective channels of the plurality of channels to cause each of the locks to partially extend beyond the second inner surface. Each of the locks of the plurality of locks may be designed to engage a portion of the heart pump when the lock assembly is transitioned into the closed position to couple the apical connector to the heart pump.

The ring may include a first end and a second end and the handle may be designed to rotate about the first end to vary a distance between the first end and the second end of the ring. The handle may include a slot and the lock assembly may further include an arm connected at a primary end to the second end of the ring and may be designed to engage the slot of the handle at a secondary end. The second inner surface may include a sealing ring recessed area and the apical connector further may further include a sealing ring disposed partially within the sealing ring recessed area. The cylindrical housing may have a plurality of dimples designed to facilitate engagement with a support tool.

BRIEF DESCRIPTION OF THE DRAWINGS

FIGS. 2A-2E illustrate cross-sectional and perspective views of an apical connector including a sewing ring, a connector housing, a ring support, and a spring.

FIGS. 9A-9D illustrate perspective views of a collar cover together with a graft assembly positioned in the stationary receiver.

FIGS. 13A-13C illustrate perspective and exploded views of an apical assembly including a tightening assembly and a locking assembly.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

The present invention is directed to an implantable heart pump system that is particularly well-suited for use as a left ventricular assist device (LVAD). The implantable heart pump system may include an undulating membrane pump suitable for long-term implantation in a patient having end-stage heart failure. The implantable heart pump may include an apical connector with a sewing ring for safely and efficiently securing the pump inlet to the heart tissue and/or a quick connect graft connector for efficiently connecting a graft to the heart pump in a manner that maintains the integrity of the graft and permits adjustments to the graft orientation relative to the pump while maintaining a seal with the pump.

Figure 1:
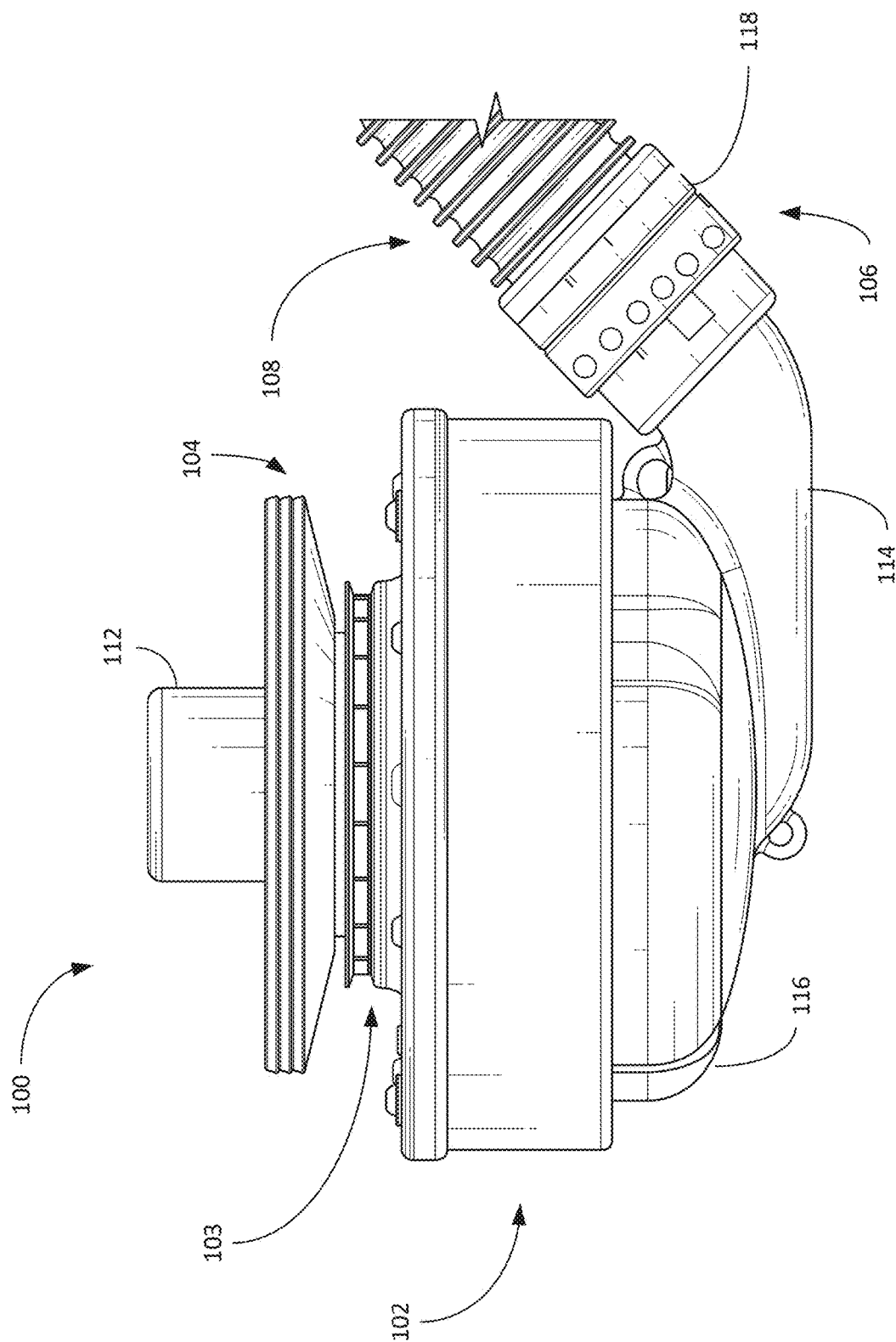
FIG. 1 illustrates a side view of exemplary implantable heart pump system including an apical connector, a sewing ring, and pump quick connector.

Referring now to FIG. 1, an exemplary implantable heart pump system is illustrated. As shown in FIG. 1, implantable heart pump system 100 may include heart pump 102, apical connector 103, sewing ring 104, pump quick connector 106, and graft connect assembly 108. Heart pump 102 may be an implantable heart pump including an undulating membrane. For example, heart pump 102 may be the implantable heart pump described in U.S. Pat. No. 10,188,779 and/or U.S. Patent Application Pub. No. 2023/0338728, the entire contents of each of which are incorporated herein by reference. In one example, heart pump 102 may be a LVAD, however it is understood that heart pump 102 may be any type of circulatory assist device.

Heart pump 102 may include pump body 116, pump inlet 112, and pump outlet 114. Pump body 116 may include an undulating membrane and may cause blood to move from pump inlet 112 to pump outlet 114. Pump inlet 112 may be cylindrical in shape and may extend from a top portion of heart pump 102. Pump inlet 112 may be designed to extend into a blood chamber of the heart (e.g., the left ventricle). Pump outlet 114 may be cylindrical or elliptical in shape to minimize pump height and may extend from a bottom portion of pump 102. Pump outlet 114 may include pump quick connector 106, which may be designed to quickly and efficiently secure the flexible graft to the pump via the graft quick connector 118, which extends from graft connect assembly 108.

Apical assembly 103 may include a central aperture having an inner diameter larger than the outer diameter of pump inlet 112. Apical assembly 103 may receive pump inlet 112 and may rest on and/or may be secured to a top portion of pump body 102. Apical assembly 103 may be the same or similar to apical assembly 200 of FIGS. 2A-2D. Apical assembly 103 may include sewing ring 104, which may be designed to receive pump inlet 112. Sewing ring 104 may be the same as or similar to sewing ring 204 illustrated in FIGS. 2A-2D. Sewing ring 104 may be made of a biocompatible material and/or may interface with heart tissue. Sewing ring 104 may be connected to the heart via one or more sutures that connect sewing ring 104 to heart tissue.

Figure 2C:
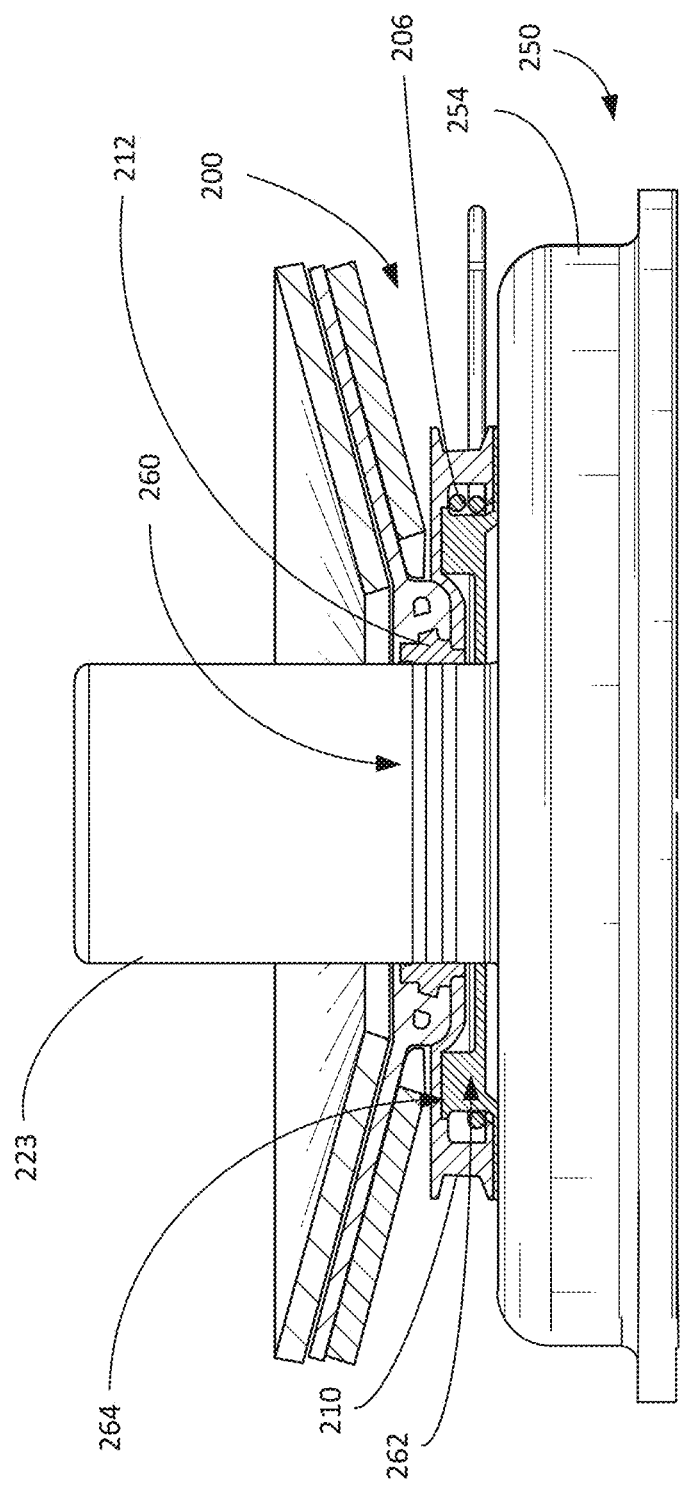

Referring now to FIGS. 2A-2D, apical assembly 200 is illustrated. Referring now to FIG. 2A, apical assembly 200 may include at least apical connector 202 and sewing ring 204. Apical connector 202 may include connector housing 210, ring support 212, and spring 206. In one example, apical connector 202 may be metallic (e.g., titanium, stainless steel, alloy, etc.). However, it is understood that apical connector 202 may be any type of rigid biocompatible material (e.g., plastic). Connector housing 210 may be annular in shape and may include a central aperture with a diameter through which the outlet or other cannula of the heart pump may be received. Connector housing 210 may include lower lip 216 and upper lip 218, which may be joined together by connector body 220. Lower lip 216 may have an interior diameter that may be larger than an interior diameter of upper lip 218. Connector housing 210 may have a diameter larger than that of the central aperture.

Spring 206 may be positioned within connector housing 210 between lower lip 216 and upper lip 218. Spring 206 may include a circular portion (e.g., expandable portion) connected to tabs 205, which may be a handle portion used to apply force to spring 206 to change the diameter. For example, tabs 205 may be forced to move together to apply increase the diameter of spring 206 to allow insertion of the pump inlet. Spring 206 may be designed so that when no force is applied to tabs 205, spring 206 applies a constrictive force onto the outer diameter of pump inlet 112 of FIG. 1 (e.g., when spring 206 transitions from an expanded position to a constricted position). For example, spring 206 may interface with a protrusion or other portion of the heart pump. After pump insertion into a heart chamber, application of force to tabs 205 release the constrictive force of spring 206 on pump inlet 112, so that the pump orientation and/or depth of penetration into the heart chamber may be adjusted based diagnostic imaging, e.g. echocardiography, fluoroscopy, or other means. Once the pump inlet has been properly positioned, the force applied to tabs 205 may be released, so that spring 206 will secure the axial orientation and position of the pump inlet. Tabs 205 may include indentation features to enable the compressive force applied to the tabs to draw them together to be applied by a suture tied between the two tabs. In this implementation, the suture tying tabs 205 together, maintains the spring 206 in an open position, permitting insertion of pump inlet 112. O-rings or other sealing features on pump inlet 112, may temporarily maintain the position of the pump inlet 112 by friction with the inner diameter of ring support 212. With the temporary connection, the surgeon may adjust the pump position and orientation. Once in the optimal position, the surgeon may cut the sutures tying tabs 205 together, releasing the restraint on spring 206, which will then return to its native confirmation, applying a constrictive force on pump inlet 112. Tabs 205 may extend outside of connector housing 210 via windows 207 in connector housing 210. Spring 206 may be designed to transition between an upper portion and a lower portion such that a portion of the spring is positioned near upper lip 218 and a different portion of the spring is simultaneously positioned near a lower lip 216. Accordingly, spring 206 may be secured within connector housing 210.

Connector housing 210 may be designed to support and/or connect to ring support 212. For example, ring support 212 may be connected and/or affixed to apical connector 202 via any well-known connection (e.g., threaded connection, welding, friction fit, etc.). Ring support 212 may be annular in shape and may include flange 230 that extends outward from ring support 212. Flange 230 may extend about the circumference of ring support 212 and may include several through-holes 232 equally spaced about flange 230. As shown in FIG. 2A, flange 230 may be angled upward and/or may be positioned above a recessed portion of upper lip 218.

Sewing ring 204 may include lower layer 241, middle layer 247 and upper layer 244. Lower layer 241 and/or upper layer 244 may be the same or different material. The lower layer 241 and upper layer 244 provide a soft fabric interface with the epicardial surface of the heart, possess excellent characteristics for retaining sutures, and which can promote local hemostasis to reduce bleeding risks. For example, lower layer 241 and/or upper layer 244 may include biocompatible felt (e.g., PTFE, Dacron, or polyester felt). Middle layer 247 may be flexible layer made from a polymer such as silicone or polyurethane, for example. Middle layer 247 may include a stiffer material than felt, to help maintain position of the pump inlet 112 in relationship to the heart chamber to which the heart pump is connected. Materials such as silicone and polyurethane typically possess poor suturability, easily tearing if a force is applied to sutures passing through such materials. However, felt materials alone lack mechanical integrity to prevent a heart pump from moving in relation to the heart chamber. This situation may result in pump inlet 112 contacting the endocardial surfaces of the heart, which can result in suction of the heart chamber wall, arrhythmias, and even mechanical erosion of the heart tissue by the pump inlet 112. The multilayer embodiment shown in FIG. 2A combines the properties of felt for suturability and tissue contact with the mechanical rigidity required to achieve improved functionality of the sewing ring 204. Sewing ring 204 may be made using an over molded technique whereby silicone or other polymer is injected or otherwise inserted (e.g., in liquid form) between upper layer 244 and lower layer and permitted to surround flange 230 and enter through-holes 232 of flange 230. The silicone may optionally be cured after being inserted and/or injected. In this manner, sewing ring 204 may be secured to ring support 212. Alternatively, or additionally, sewing ring 204 may be secured to ring support 212 using any other well-known techniques (e.g., sutures).

As shown in FIGS. 2A and 2B, sewing ring 204 may have a concave or generally concave shape. As flange 230 is angled upward, the sewing ring 204 may assume the concave shape when middle layer 247 is secured to flange 230. It is understood that that the concave shape of sewing 204 may be desirable for suturing or otherwise securing sewing ring 204 to the heart tissue at the apex of the heart. For example, the apex may be generally peaked or domed shaped such and the concave shape of sewing ring 204 may receive and/or conform to the generally peaked and/or domed shape of the apex of the heart. It is understood that the flange may assume a certain angle to cause the sewing angle to properly interface with the size and shape of the heart anatomy. Sewing ring 204 may be cut or trimmed by the implanting surgeon to the desired size, based on the size and shape of the patient heart, as well as the presence of scar tissue, calcification, or other injuries to the heart wall, which could impact suture retention or optimal pump orientation and position.

Referring now to FIG. 2B, a perspective view of apical assembly 200 is illustrated. As shown in FIG. 2B, connector housing 210 may include dimples 240 equally distributed about an outer diameter of connector housing 210 circumferentially. For example, dimples 240 may each have a radius of curvature and together may create a series of ridges 242. Dimples 240 and/or ridges 242, may be sized and shaped to receive a grasping end of forceps. In one example, forceps may be specifically designed to include end portions sized and shaped to mate with dimples 240. It is understood that forceps may be used to grasp apical assembly 200 for implanting apical assembly and/or the heart pump at the heart. FIG. 2B further illustrates windows 207, which permit tabs 205 to exit connector housing 210.

Referring now to FIG. 2C, perspective cutaway view of apical assembly 200 is illustrated on heart pump 250. Heart pump 250 may be the same or similar to heart pump 102 of FIG. 1. As shown in FIG. 2C, heart pump 250 may include inlet 223 and top portion 254, which may support and/or be connected to connector housing 210. Inlet 223 may include one or more (e.g., two, three, four, etc.) sealing rings 260. For example, inlet may include multiple sealing ring recesses (e.g., semi-circular indentations) designed to receive a portion of a sealing ring. Sealing rings 260 and/or corresponding indentations may be positioned at various heights along inlet 223. For example, sealing rings 260 and/or corresponding indentations may be positioned near the bottom of inlet 223, as shown in FIG. 2C.

Sealing rings 260 may be any well-known sealing-ring and/or O-ring or the like. One or more sealing rings 260 may interface with ring support 212 to create a seal that extends 360 degrees to prevent any fluid from escaping or leaking from the heart chamber. Ring support 212 may have an internal surface that is flat and/or smooth for maximizing contact with sealing rings 260. While one sealing ring 260 may be sufficient to create a seal with ring support 212, it is understood that multiple sealing rings positioned along inlet 223 to provide multiple height options for apical assembly 200 along inlet 223. For example, depending on the patient's anatomy, it may be desirable to mate ring support with a sealing ring higher or lower on inlet 223.

Pump 250 may include receiving portion 262 which may extend or otherwise protrude from top portion 254 of heart pump 250. It is understood that receiving portion 262 may interface with spring 206 and/or connector housing 210 and may have an extended height for greater manipulation of the height of ring support 212 with respect to inlet 223. Receiving portion 262 may be cylindrical and/or annular in shape and may be sized to have an outer diameter that is receiver by the inner diameter of connector housing 210. An outer diameter of receiving portion 262 may optionally include upper flange which may be designed to resist upward movement of spring 206 beyond a certain point. Spring 206 may be biased to close (e.g., decrease in diameter) and thus may be biased to clamp or otherwise grip receiving portion 262. As spring 206 is constrained from moving upward with respect to flange 230 and spring is restrained within connector housing 210, spring 206 may secure connector housing 210 and therefore apical assembly 200 to heart pump 250. Receiving portion 262 may have a smooth surface to maximize contact and thus friction with spring 206.

Figure 2D:
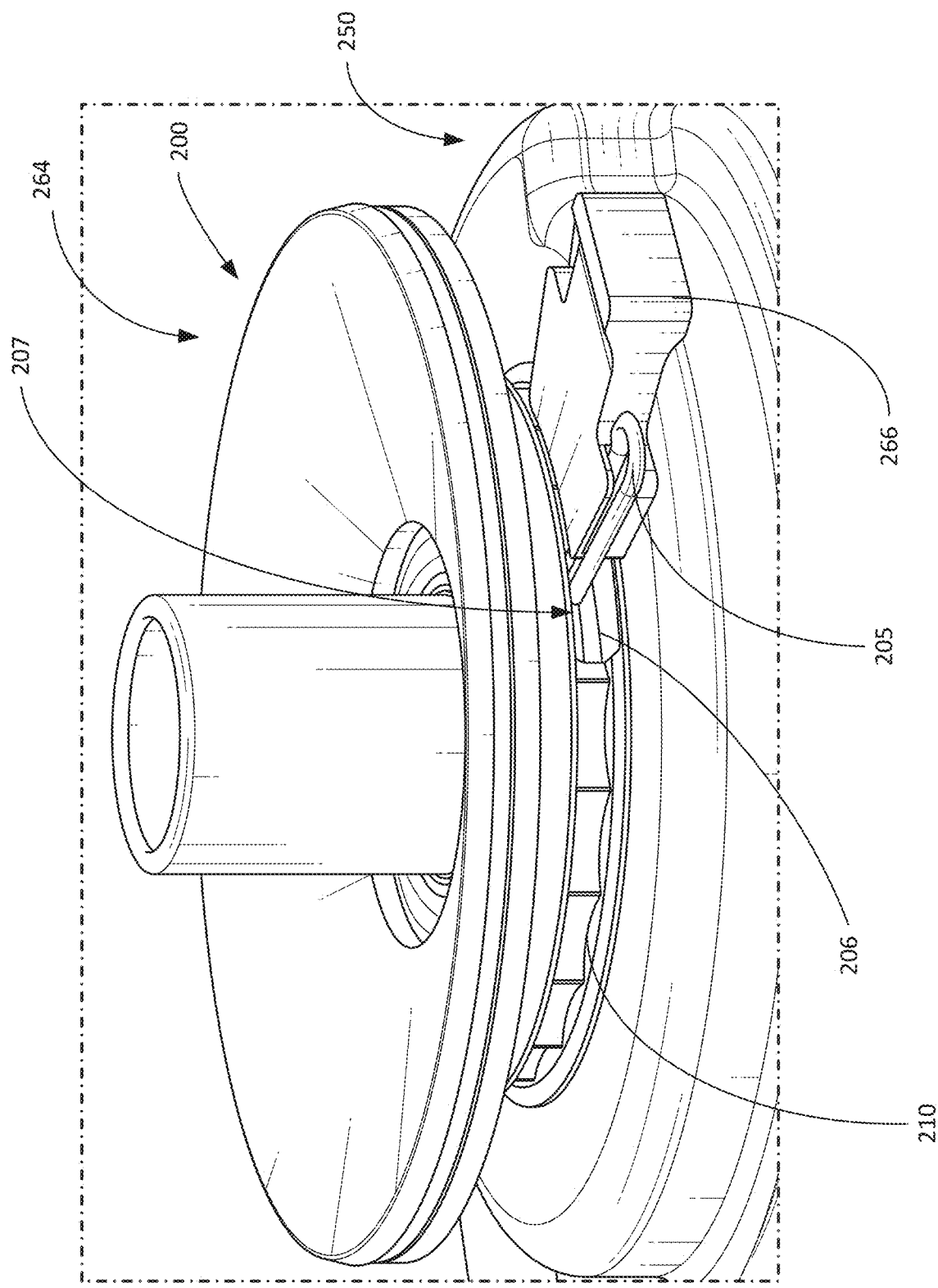

Referring now to FIG. 2D, perspective view of apical assembly 200 is illustrated on heart pump 250. As shown in FIG. 2D, tab 205 extending from spring 206 exits window 207 of connector housing 210. Tabs 205 may be locked into place such that they may not be moved closer to one another to increase the diameter of spring 206. For example, lock 266 may be designed to receive both of tabs 205 and prevent each tab from moving closer to the other tab. Lock 266 may also be designed to exert a force displacing tabs 205 further apart, which thereby increases the constrictive force applied by spring 206 onto the outer diameter of pump inlet 223. The indentation features in tabs 205, previously available to be used to apply a suture to maintain spring 206 in an open position to facilitate pump insertion and optimal positioning, may serve as retention features to secure lock 266 in place. Lock 266 is inserted onto tabs 205 through slots into the sides of lock 266. The angular width of lock 266 in relation to the central axis of apical assembly 200 determines the amount of additional constrictive force applied by spring 206 on pump inlet 223. By preventing spring 206 from increasing in diameter, lock 266 may lock spring 206 and thus apical assembly 200 into place with respect to pump 250.

Figure 2E:
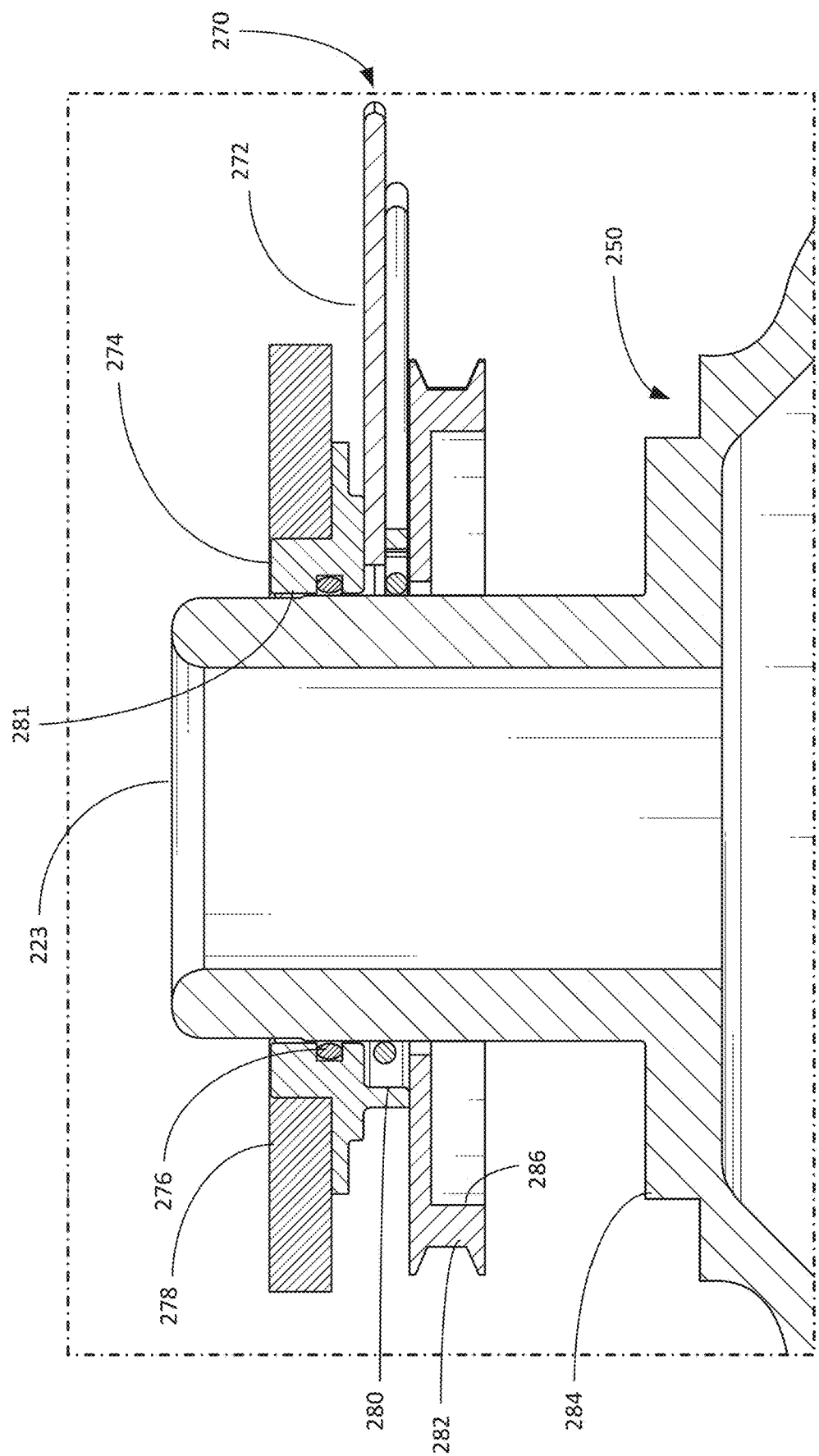

Referring now to FIG. 2E, a cross-sectional view of heart pump 250 and apical assembly 270 is illustrated, which may be similar to apical assembly 200 of FIG. 2A. Apical assembly 270, like apical assembly 200 of FIG. 2A may include a sewing ring (e.g., sewing ring 278) to secure the apical assembly to heart tissue. Sewing ring 278 may be the same or similar to sewing ring 204 of FIG. 2A and may either be flat, as shown in FIG. 2E or concave as shown in FIG. 2A. For example, sewing ring 278 may include the same three layer structure as sewing ring 204 of FIG. 2A. Ring support 274 may include a flange with through-holes or alternatively may include a flange with protrusions for securing the polymer layer of sewing ring 278 to ring support 274.

Ring support 274 may further include lower recessed portion 280 with an interior diameter larger than upper interior diameter 281 of ring support 274 designed to interface with inlet 223. Lower recessed portion 280 may be designed to receive spring 272, which may be similar to spring 206 of FIG. 2A and may be designed to clamp or otherwise grasp an exterior of inlet 223. It is understood that inlet 223 may alternatively be an outlet or any other cannula of a blood pump (e.g., heart pump).

Ring support 274 may, at a bottom portion of ring support 274, interface with and/or connect to connector housing 282. Connector housing 282 may include opening 286 near the bottom of connector housing 282, which may include an interior diameter and/or interior surface designed to receive, conform to, and/or mate with top portion 284 of the heart pump. Connector housing 282 may connect to ring support 274 via any well-known connection (e.g., threaded connection, welding, friction fit, etc.). As shown in FIG. 2E, ring support 274 may include sealing ring 276 which may be similar to sealing ring 260 of FIG. 2C, but may be positioned into a recessed portion of ring support 274. Alternatively, or additionally, inlet 223 may include sealing rings 260 for creating a seal between ring support 274 and inlet 223.

Figure 3B:
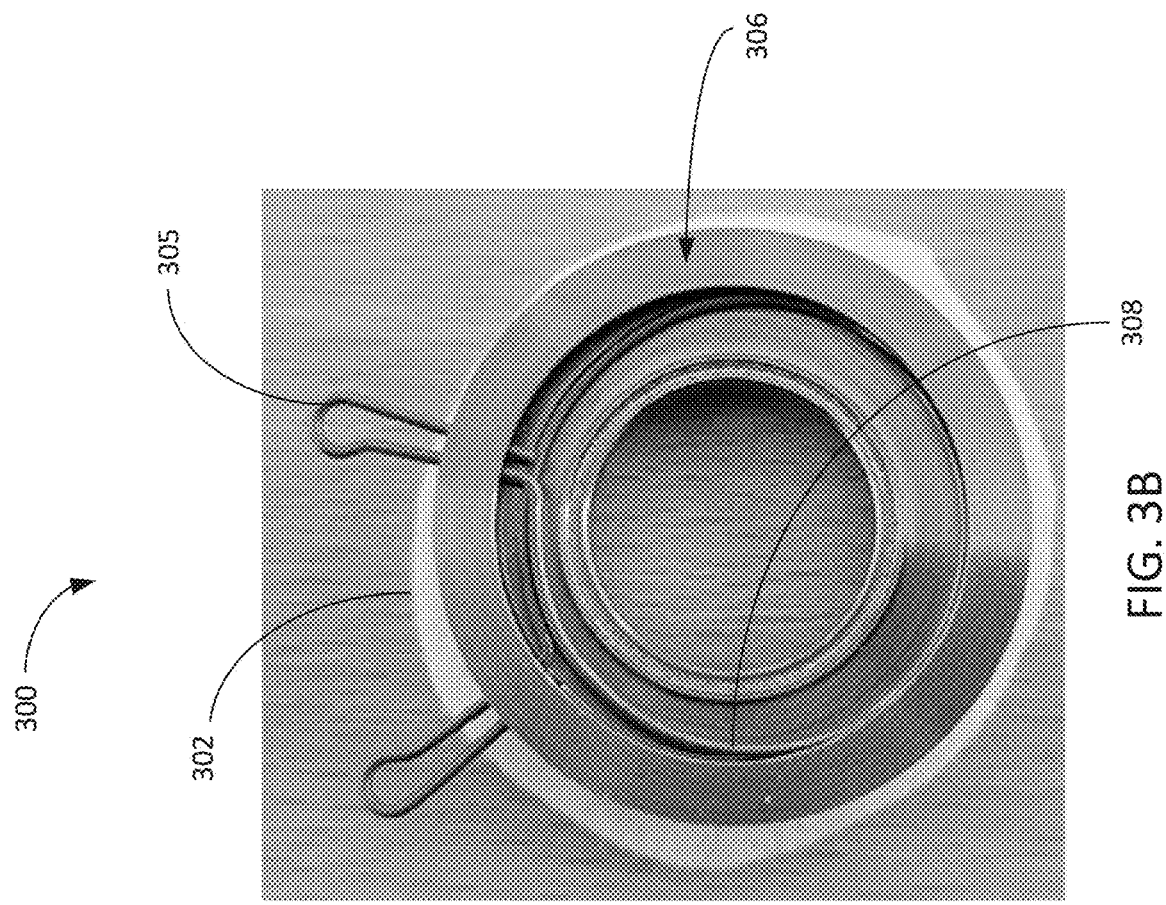
FIGS. 3A-3C illustrate top and bottom views of an apical connector including a sewing ring, a connector housing, a ring support, and a spring, as well a perspective view of the spring.
Figure 3A:
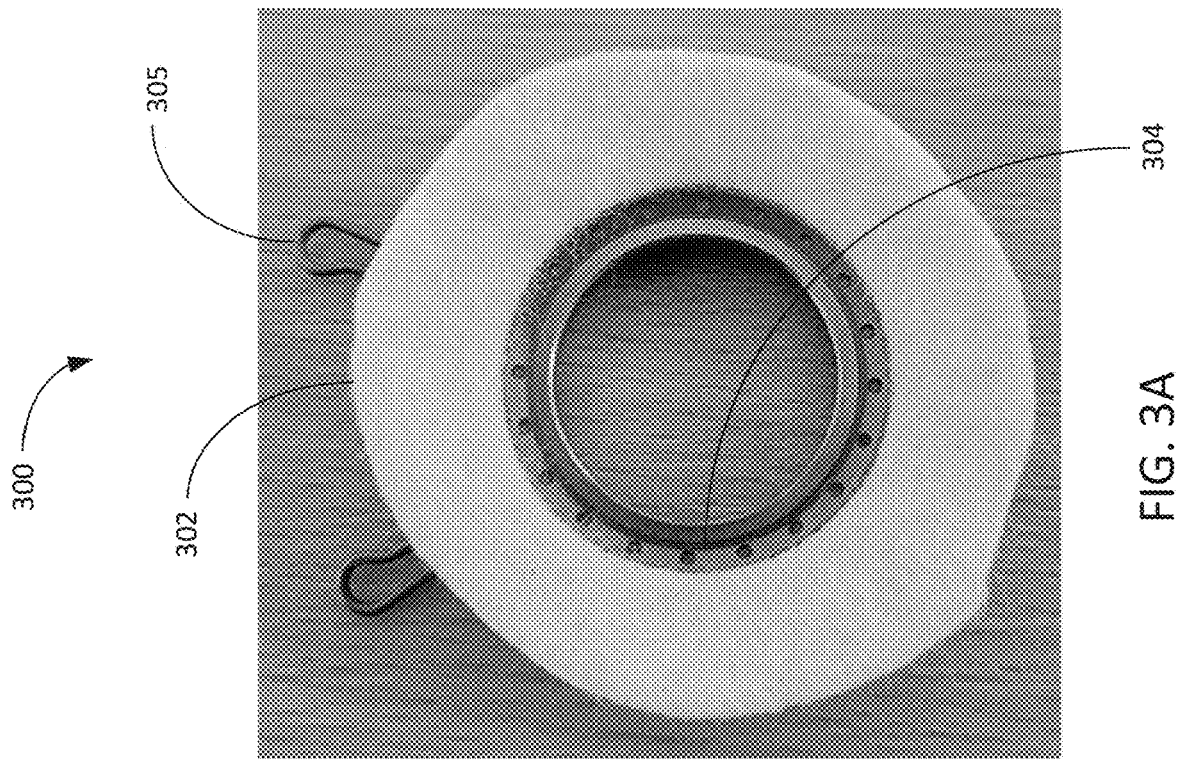

Referring now to FIGS. 3A-3B, apical assembly 300 is illustrated. Apical assembly 300 may be the same or similar to apical assembly 200 of FIG. 2A. For example, apical assembly 300 may include sewing ring 302, which may be the same or similar to sewing ring 204 of FIG. 2A, ring support 304, which may be the same or similar to ring support 230, connector housing 306, which may be the same or similar to connector housing 210 of FIG. 2A, and spring 308 and tabs 305, which may be the same or similar to spring 206 and tabs 205 of FIG. 2A.

Figure 3C:
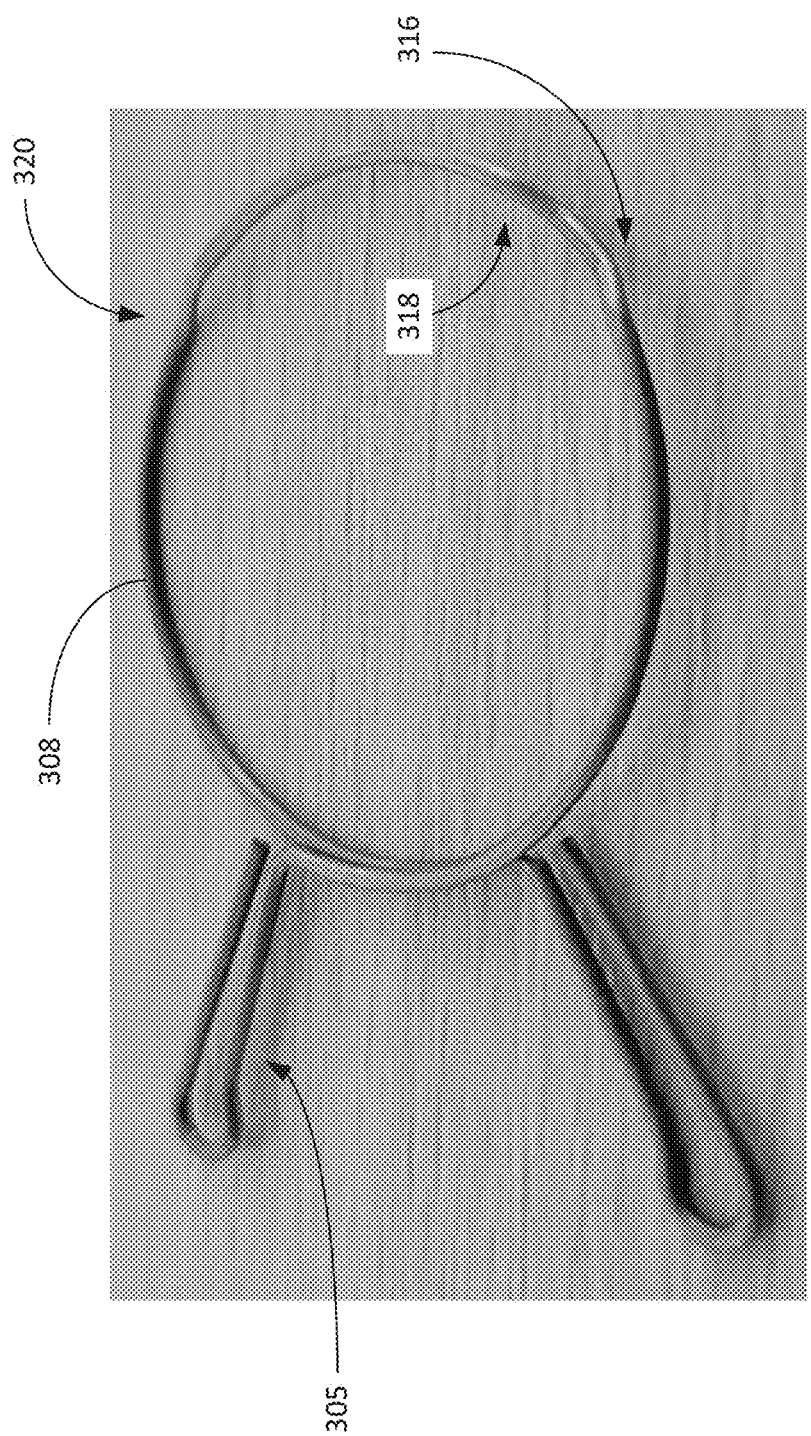

Referring now to FIG. 3C, spring 308 is illustrated. As shown in FIG. 3C, spring 308 may include tabs 305 for increasing the diameter of spring 308. Spring 308 may include feature 316, feature 318 and feature 320. Spring 308 may extend generally along a plane and feature 316 may cause spring 308 to move downward in a direction generally perpendicular to the plane, feature 318 may cause spring 308 to move upward in a direction generally perpendicular to the plane, and feature 320 may cause spring 308 to move downward in a direction generally perpendicular to the plane. The variation in height of the spring caused by features 316, 318, and 320 may cause spring to maintain its position with respect to the connector housing in which it is positioned.

Figure 4A:
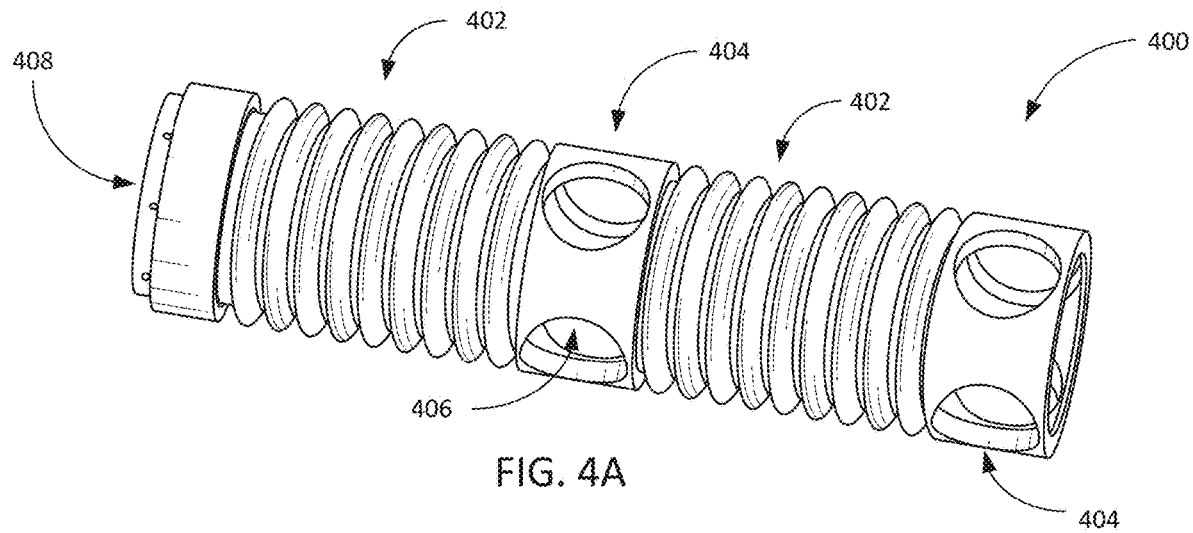
FIGS. 4A-4C illustrate perspective and cross-sectional views of a support tube and a graft tube.
Figure 4B:
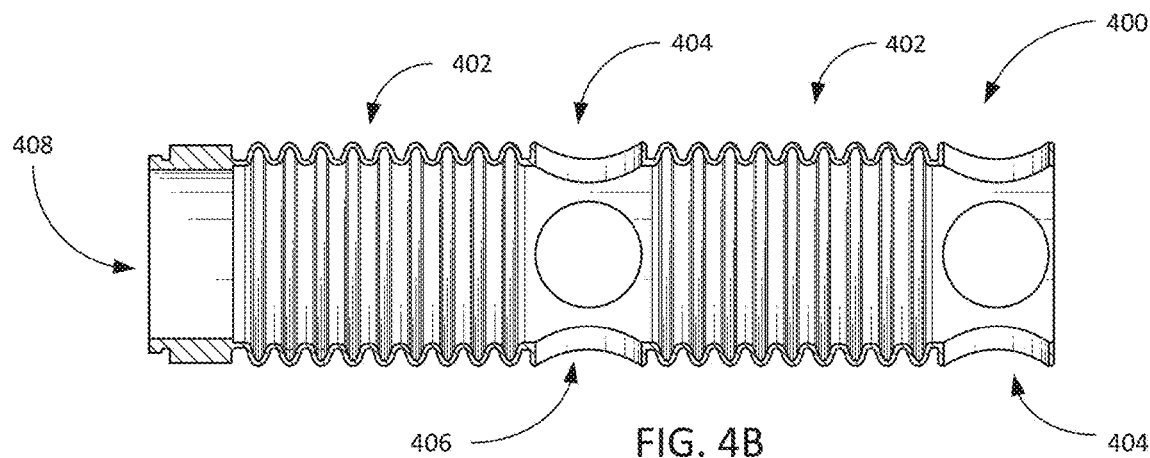
Figure 4C:
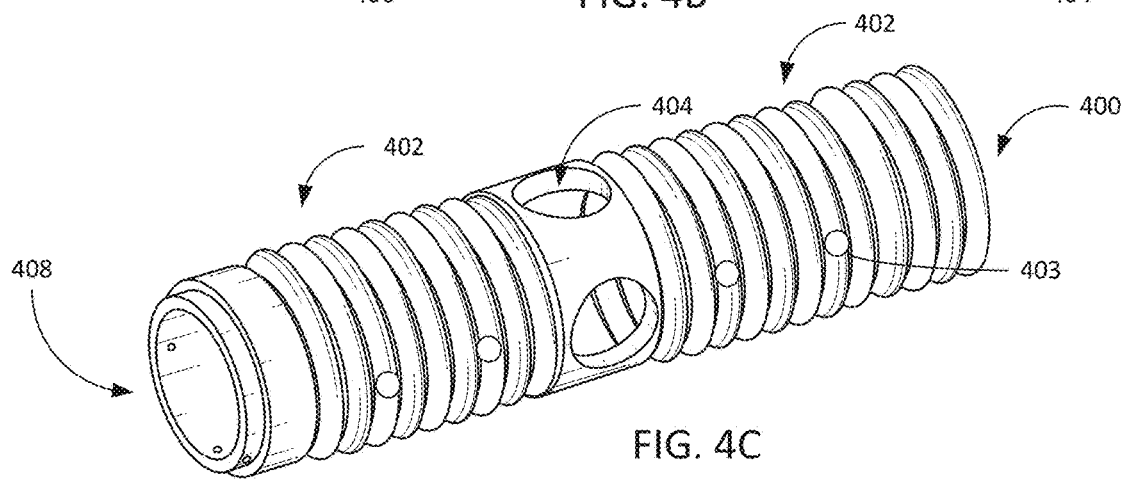

Referring now to FIGS. 4A-4C, support tube 400 is illustrated. Support tube 400 may provide rigidity and support to at least a portion of a flexible fabric tube, i.e. graft tube, extending from an outlet of the heart pump. Support tube 400 may be cylindrical in shape and may be made from any well-known biocompatible polymer or plastic. Support tube may be designed to be placed externally to surround a graft tube that may extend from the outlet of the pump to the patient's circulatory system (e.g., aortic arch). Support tube 400 may be designed to be attached to the pump outlet or pump body to maintain the axial position of the support tube 400 in relation to the graft tube. The graft tube may be made of any known fabric and/or polymer material, for example Dacron or ePTFE.

The graft tube may be permitted to bend and/or may be flexible. As the graft tube may be flexible, it may be vulnerable to kinking and/or compressing such that blood flow through the graft may be obstructed. The risk of kinking is high near the outlet of the heart pump as the heart pump outlet is rigid and the graft may be redirected upward (e.g., towards the aortic arch) immediately after the connection with the outlet, which may cause the graft to crease or kink. To avoid blood flow obstruction in the graft tube, support tube may be positioned over the graft tube.

Support tube 400 may include one or more pleated sections 402, which may have an accordion-type structure. For example, pleated sections 402 may be designed to expand and/or contract in length. Grip sections 404 may be positioned between pleated sections 402. Grip sections 404 may be annular in shape and may include relatively large though holes 406, which may have diameters that span nearly the entire length of grip sections 404. Though holes 406 may be sized such that a user's fingertips or surgical instruments may easily interface with through-holes 406 to grip and/or turn support tube 400. Grip sections 404 may also be designed provide strain relief, to flex longitudinally, and/or twist about the longitudinal axis of support tube 400. Holes 406 may optionally be big enough for a surgeon or other healthcare provider to pinch the graft or to employ surgical instrument to compress or stabilize the graft to express biological fluid through the graft and/or deliver a needle and/or suture to the graft to remove air or release certain biological fluid build up within the graft.

Figure 6:
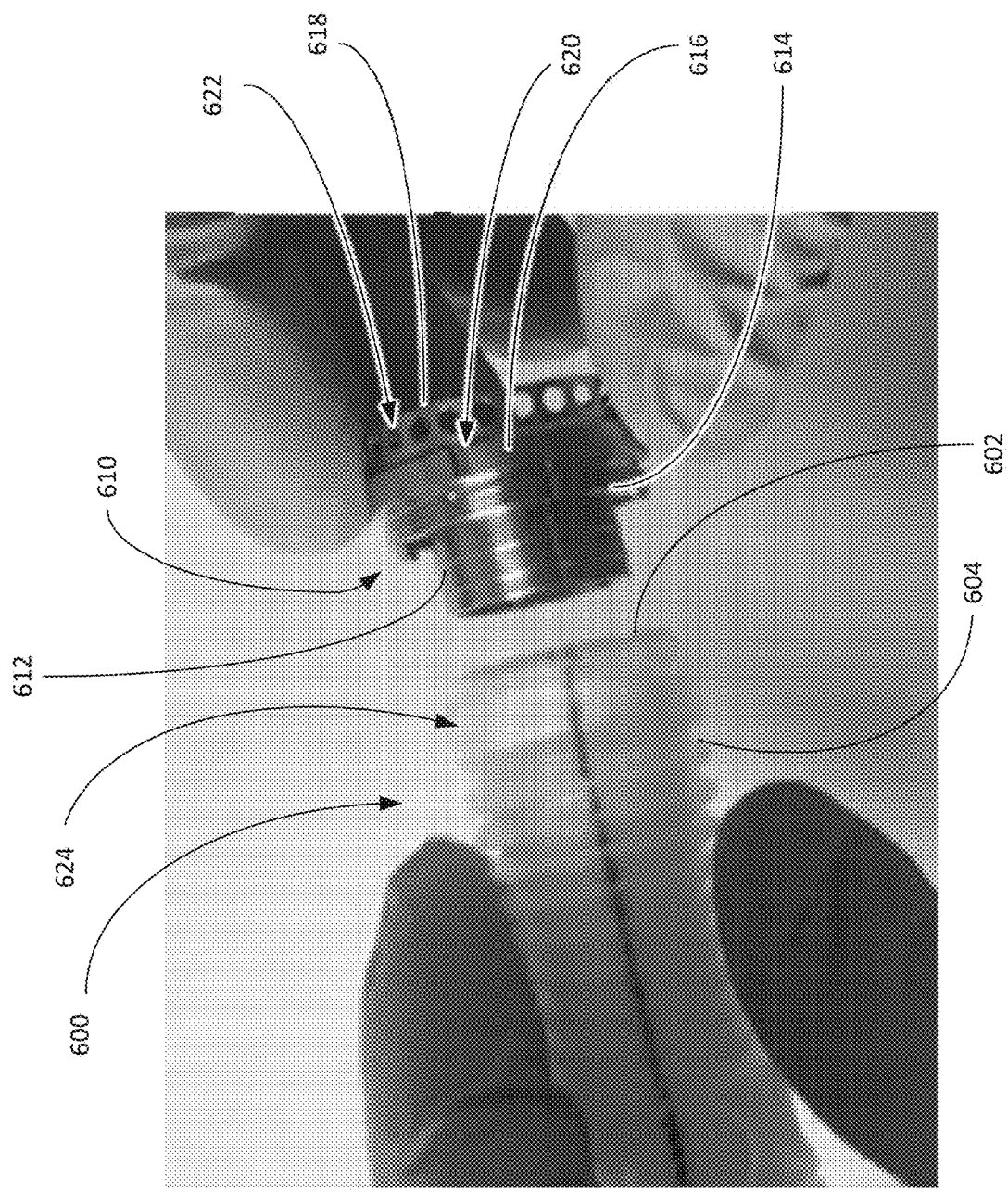
FIG. 6 illustrates a preservative view of a graft quick connect assembly and a graft assembly.

Support tube 400 may further include connector section 408, which may be annular in shape. Connector section 408 may be connected to the graft tube. For example, connector section 408 may be sutured or otherwise adhered to the graft tube, which may be positioned within an interior surface of support tube 400. In one example, a needle may be positioned through connector section 408 such that a suture can connect connector section 408 to the graft tube. Connector section 408 may be connected to a quick connect mating structure on an exterior surface and below an interior surface of connector section 408, as illustrated in FIG. 6.

Referring to FIG. 4C, holes 403 may be positioned along pleated section 402. For example, four rows of holes 403 may be equally spaced longitudinally along support tube 400. It is understood that holes 403 may be smaller than holes 406. Holes 403 may permit any fluid collecting on the tube or seeping through the graft tube to escape via holes 403. For example, the graft tube may be fabric or otherwise semi-porous and biological fluid may seep through the graft tube. In the absence of such holes, biological fluid seeping through the wall of the graft tube may accumulate between the support tube 400 and graft tube, resulting in compression and obstruction of graft tube.

Figure 5A:
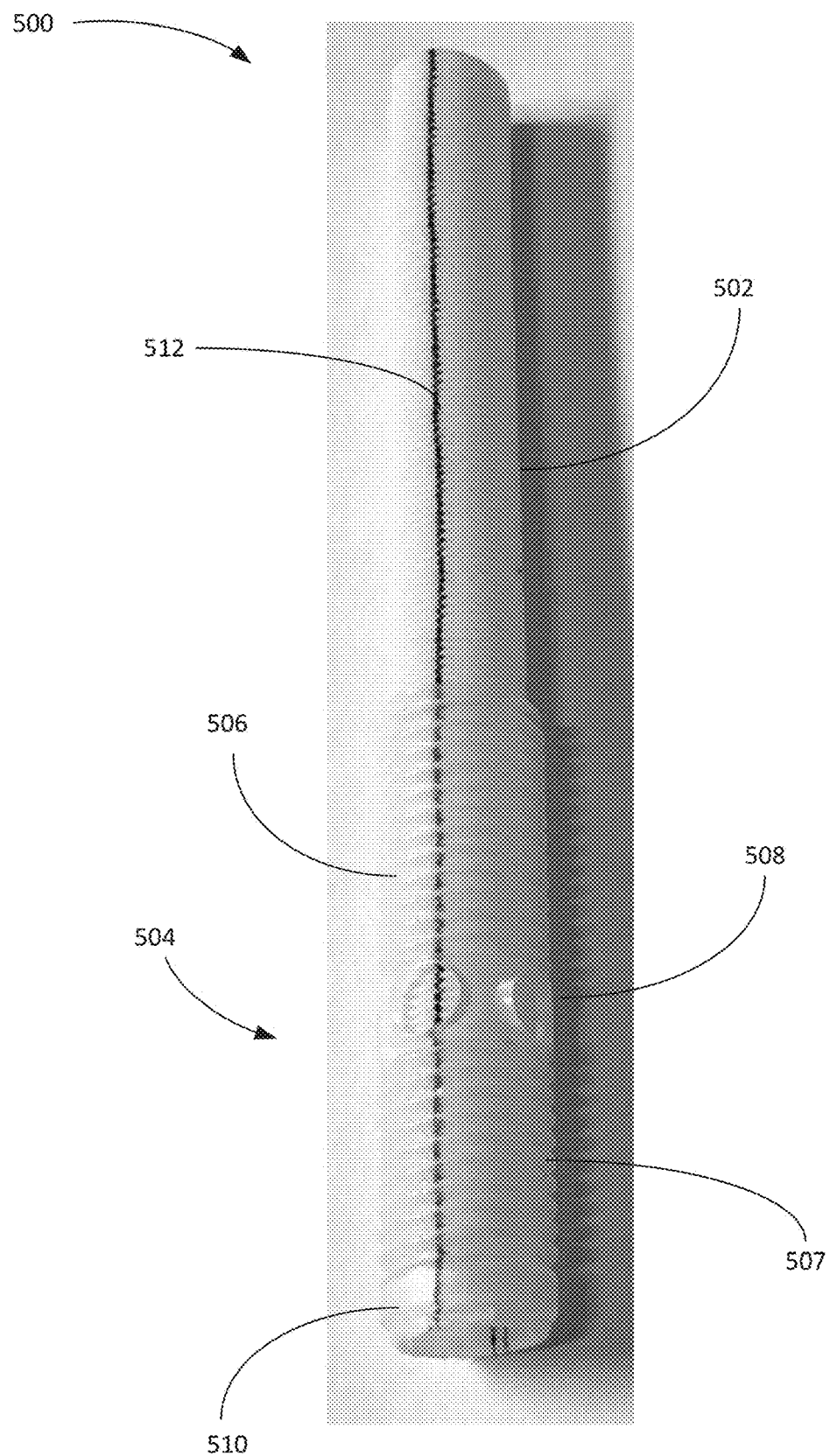
FIGS. 5A-5C illustrate views of a graft tube connected to a support tube via multiple sutures.
Figure 5B:
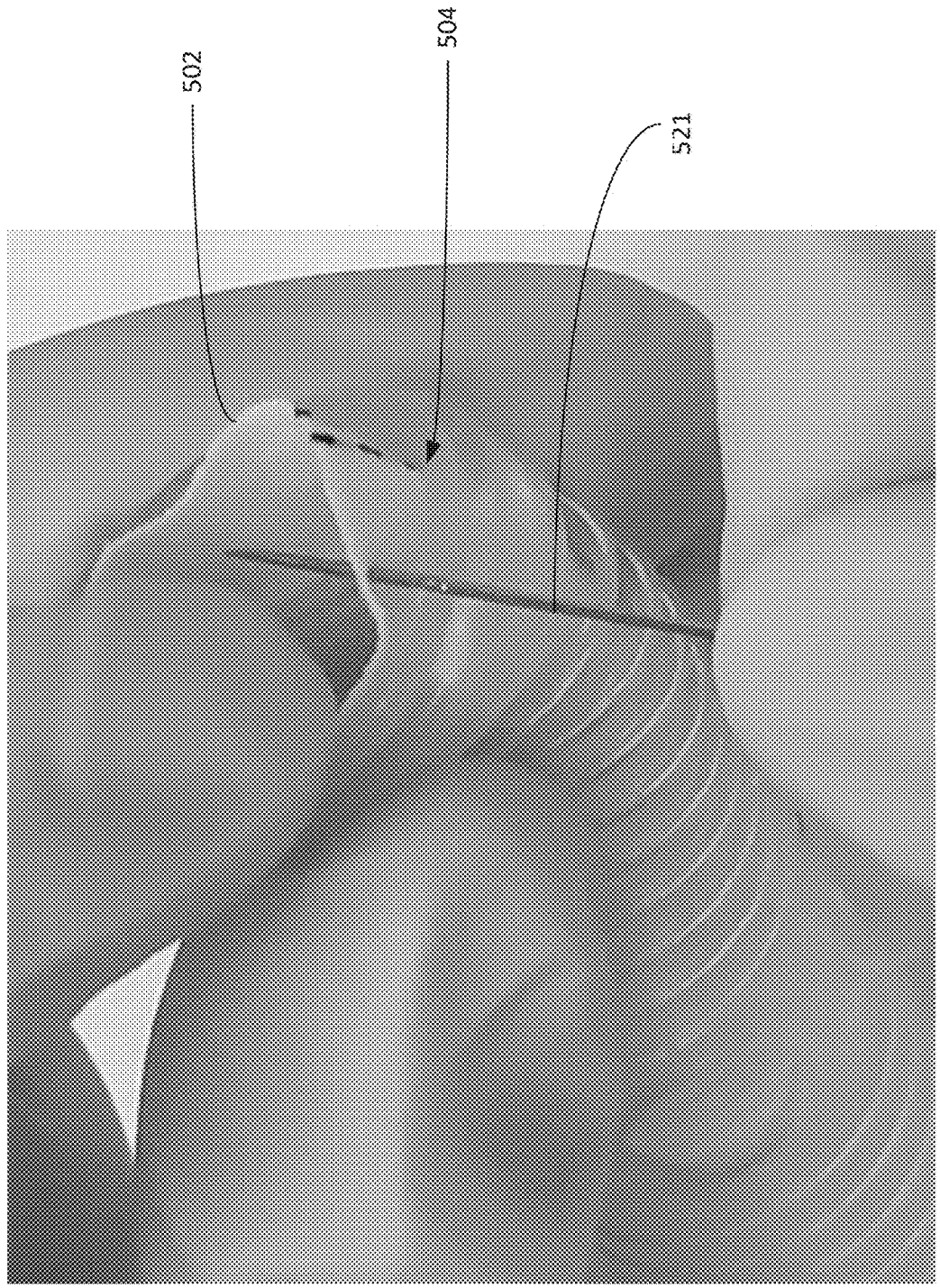
Figure 5C:
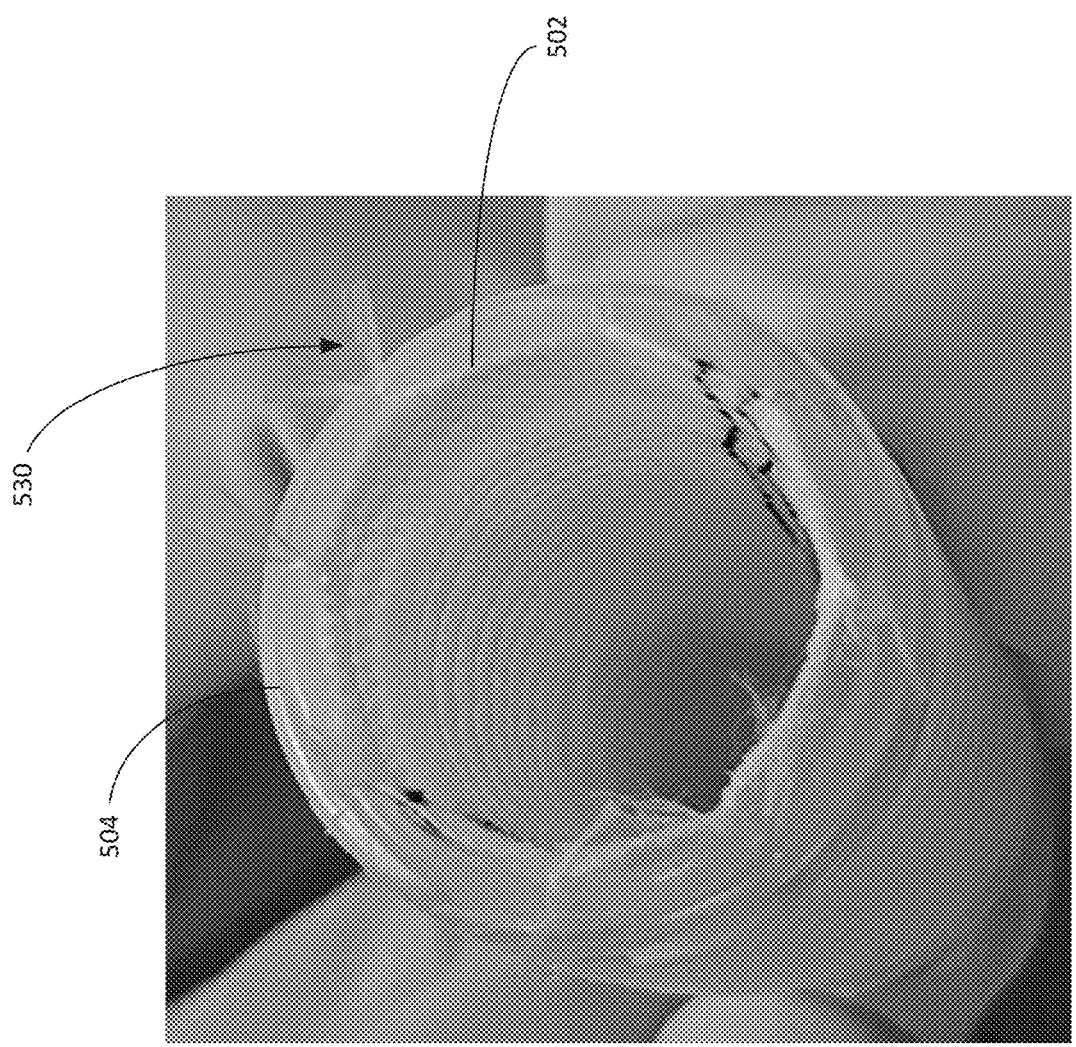

Referring now to FIGS. 5A-5C, graft assembly 500 may include graft tube 502 and support tube 506. Graft tube 502 may have a smaller diameter than support tube 504 and may be positioned within support tube 504. Support tube 506 may be the same or similar to support tube 400 of FIGS. 4A-4C. For example, support tube 506 may include grip section 508, which may be the same or similar to grip sections 404 of FIGS. 4A-4C. Further, support tube 506 may include pleated sections 507, which may be corrugated, and connector section 510, which may be the same as or similar to pleated sections 402 and connector section 408 of FIGS. 4A-4C.

Graft tube 502 may be tubular in shape and may have an accordion structure to facilitate flexing, turning, and twisting movements. In one example, graft tube 502 may be made from any well-known polymer, fabric, plastic or the like. Graft tube 502 may include one or more lines 512, extending longitudinally along graft tube 502. Line 512 may indicate a degree of twist or rotation of graft tube 502. For example, a surgeon or other healthcare technician connecting the graft tube to the pump outlet and/or circulatory system of the patient may quickly know the degree to which graft tube 502 is twisted and/or bent by looking at line 512. Support tube 504 may be transparent such that line 512 may be visible through support tube 504.

Referring now to FIGS. 5B and 5C, a first end of support tube 504 may be sutured to a first end of graft tube 502 while graft tube 502 is positioned within support tube 504. For example, needle 521 may puncture both support tube 520 and graft tube 502, and may be used to connect graft tube 502 to support tube 504 using sutures (e.g., sutures 530). Alternatively, graft tube 502 may be connected to support tube 504 via any other well-known method (e.g., adhesion, melting, sintering, etc.).

Referring now to FIG. 6, graft assembly 600 including support tube 604 and graft tube 602 may be mated with graft quick connect assembly 610, which may be one integrated piece or made of several pieces connected together (e.g., welded, threaded, or otherwise affixed). Graft assembly 600, support tube 604, and graft tube 602 may be the same as or similar to graft assembly 500, support tube 504, and graft tube 502 of FIG. 5. Graft quick connect assembly 610 may include interior flange 612, outer flange 614, which may be threaded, outer surface 616, which include one or more indentation 620, and connector flange 618, which may include several holes 622 extending therethrough.

Interior flange 612 may extend within an interior diameter of graft tube 602 and outer flange 614 may extend over an outer diameter of support tube 604. In one example, support tube 604 may include connector section 624, which may be sized to friction fit between interior flange 612 and outer flange 614. Graft quick connect assembly 610 may be made from metal (e.g., titanium, stainless steel, alloy, etc.) and/or any other material having rigid properties resistive to tensile forces (e.g., plastic).

Figure 7A:
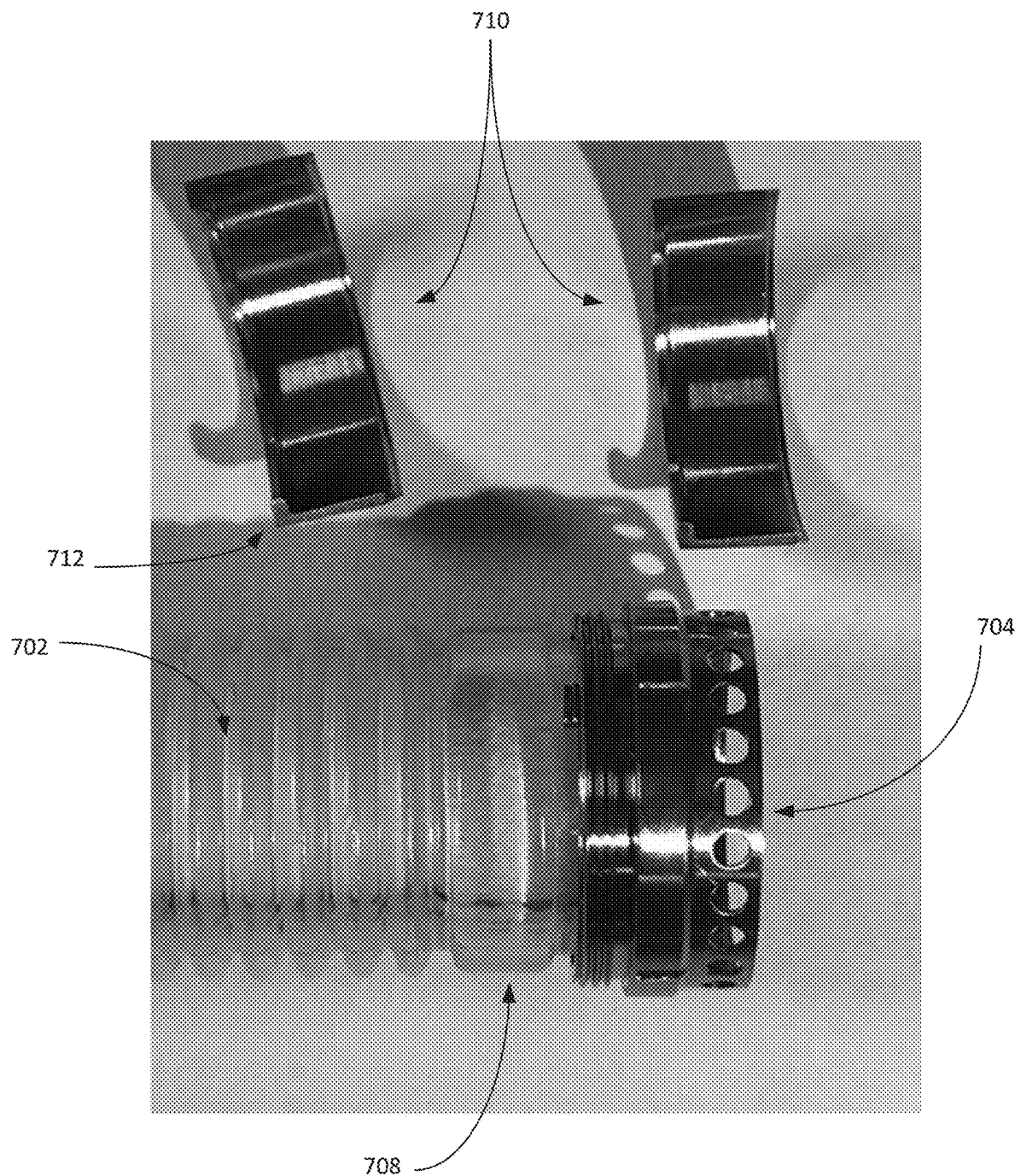
FIGS. 7A-7B illustrate perspective views of a graft quick connect assembly connected to a graft assembly.
Figure 7B:
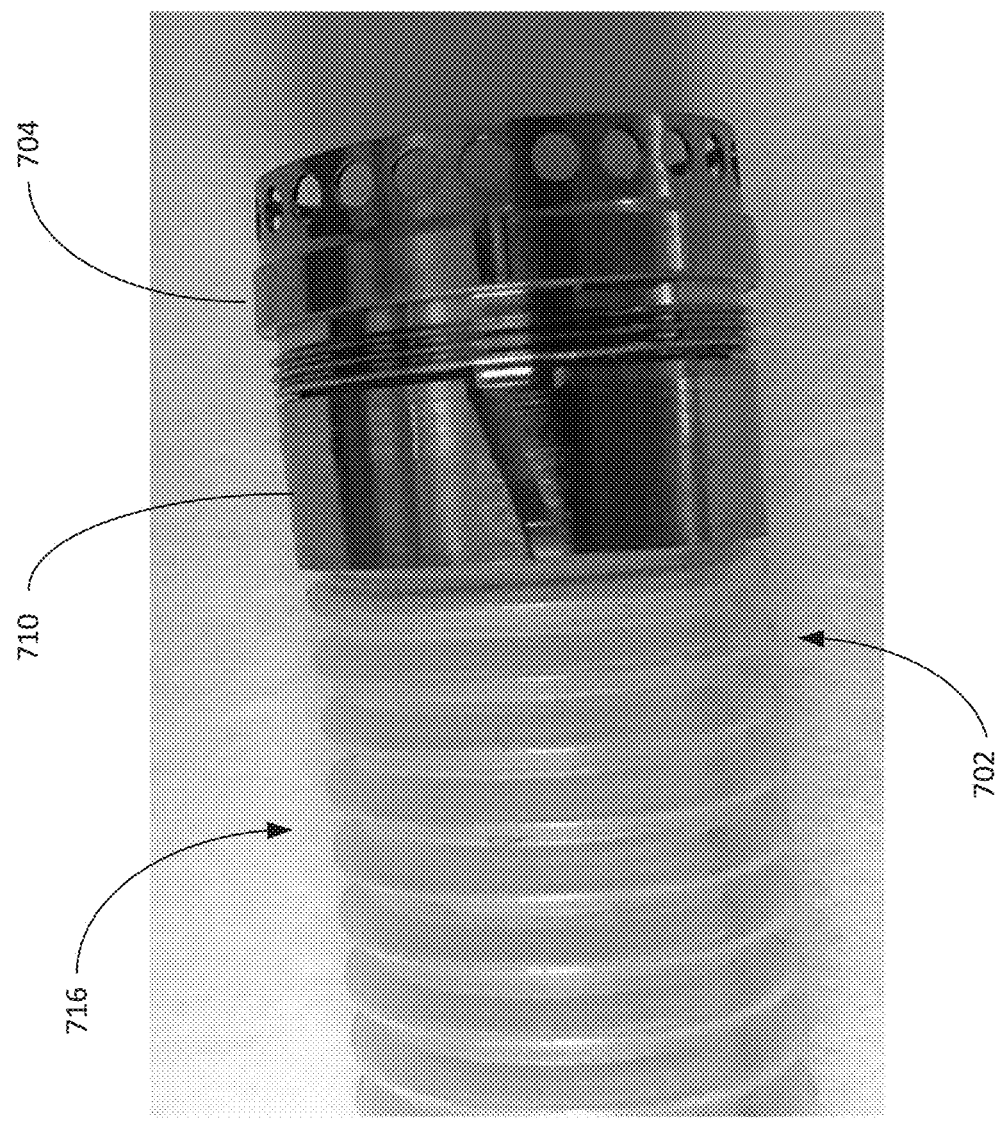

Referring now to FIGS. 7A-7B, collar 715 and graft assembly 702 together with graft quick connect assembly 704 are illustrated. Graft assembly 702 and graft quick connect assembly 704 may be the same as or similar to graft assembly 600 and graft quick connect assembly 610 of FIG. 6. Collar 710 may be split in two pieces. Collar 710 may be positioned onto connector section 708, which may be flat for a length equal to or similar to the length of collar 710. Collar 710 may include flange 712 which may extend inward from an inner diameter of collar 710.

Referring now to FIG. 7B, collar 710 is illustrated positioned onto graft assembly 702 adjacent to graft quick connect assembly 704. As shown in FIG. 7B, collar 710 may form an annular structure that may be positioned on connector section of graft support of graft assembly 702. The flange of collar 710 may be positioned furthest from graft quick connect assembly 704 and may be designed to fill a space between the connector section and the pleated section.

Figure 8A:
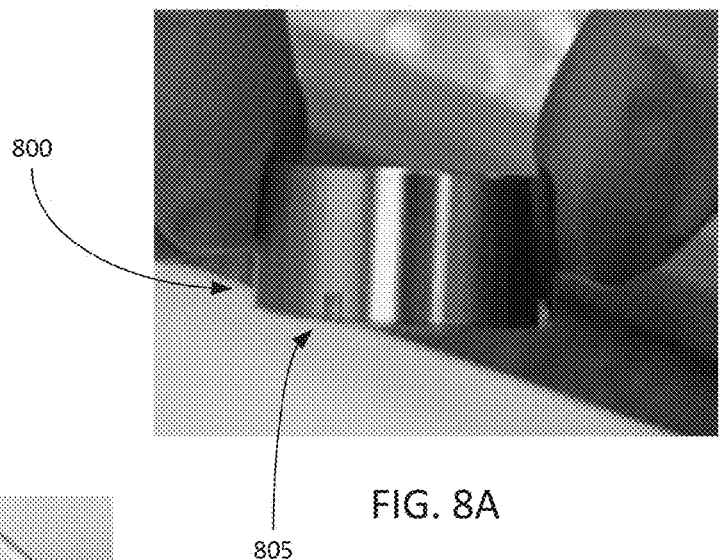
FIGS. 8A-8C illustrate perspective views of a collar cover and a stationary receiver.
Figure 8B:
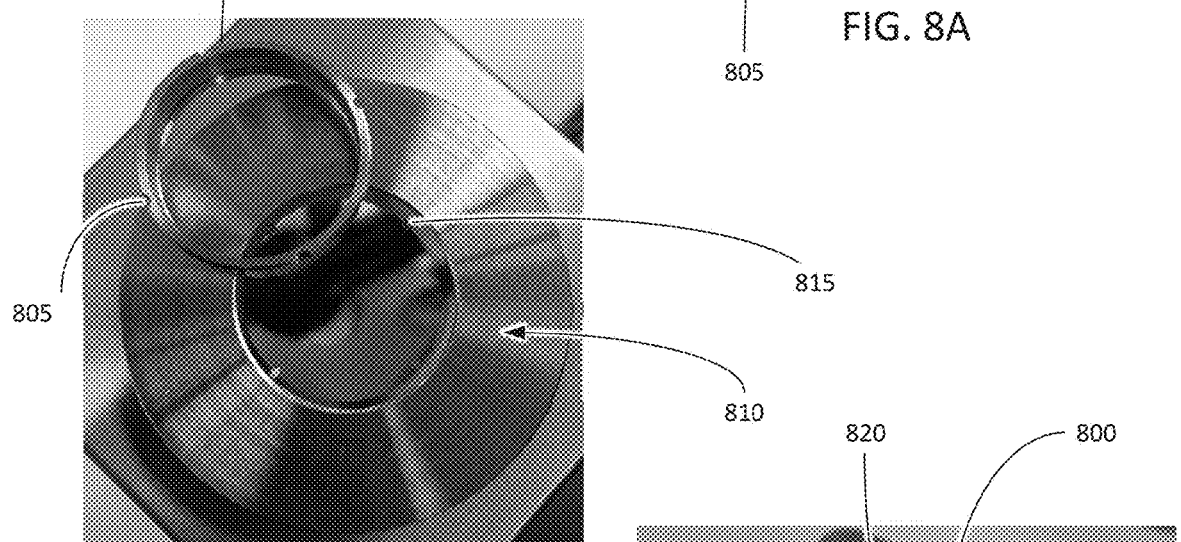
Figure 8C:
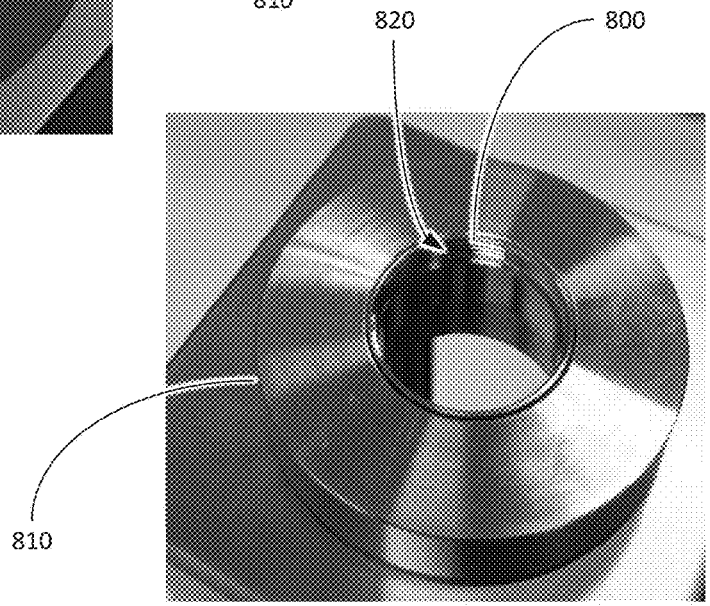

Referring now to FIGS. 8A-8C, collar cover 800 and stationary receiver 810 are depicted. Collar cover may be placed over collar 710 of FIG. 7B. Collar cover 800 may include indentations 805 which may be four indentations and/or recessions in collar cover 800, equally spaced about the circumference of collar cover 800 at the bottom of collar cover 800. Collar cover 800 may be inserted into stationary receiver 810, which may have a through-hole with an internal diameter sized to receive the outer diameter of collar cover 800.

Stationary receiver 810 may include in the interior diameter of the through-hole protrusions 815 near the bottom of the through-hole. Protrusions 815 may include four equally spaced apart protrusions. As shown in FIG. 8C, collar cover 800 may be sized to fit into the through-hole of stationary receiver 810 when indentations 805 of collar cover 800 are aligned with protrusions 815 of stationary receiver 810. Indentations 805 may be sized and shaped to receive protrusions 815 such that collar cover 800 fits flush with stationary receiver 810. It is understood that relative to collar cover 800, stationary receiver 810 may be stationary and/or immovable. As shown in FIG. 8C, collar cover 800 may include threaded portion 820 that may be positioned on the interior diameter of collar cover 800 on an opposite end of indentations 805.

Figure 9C:
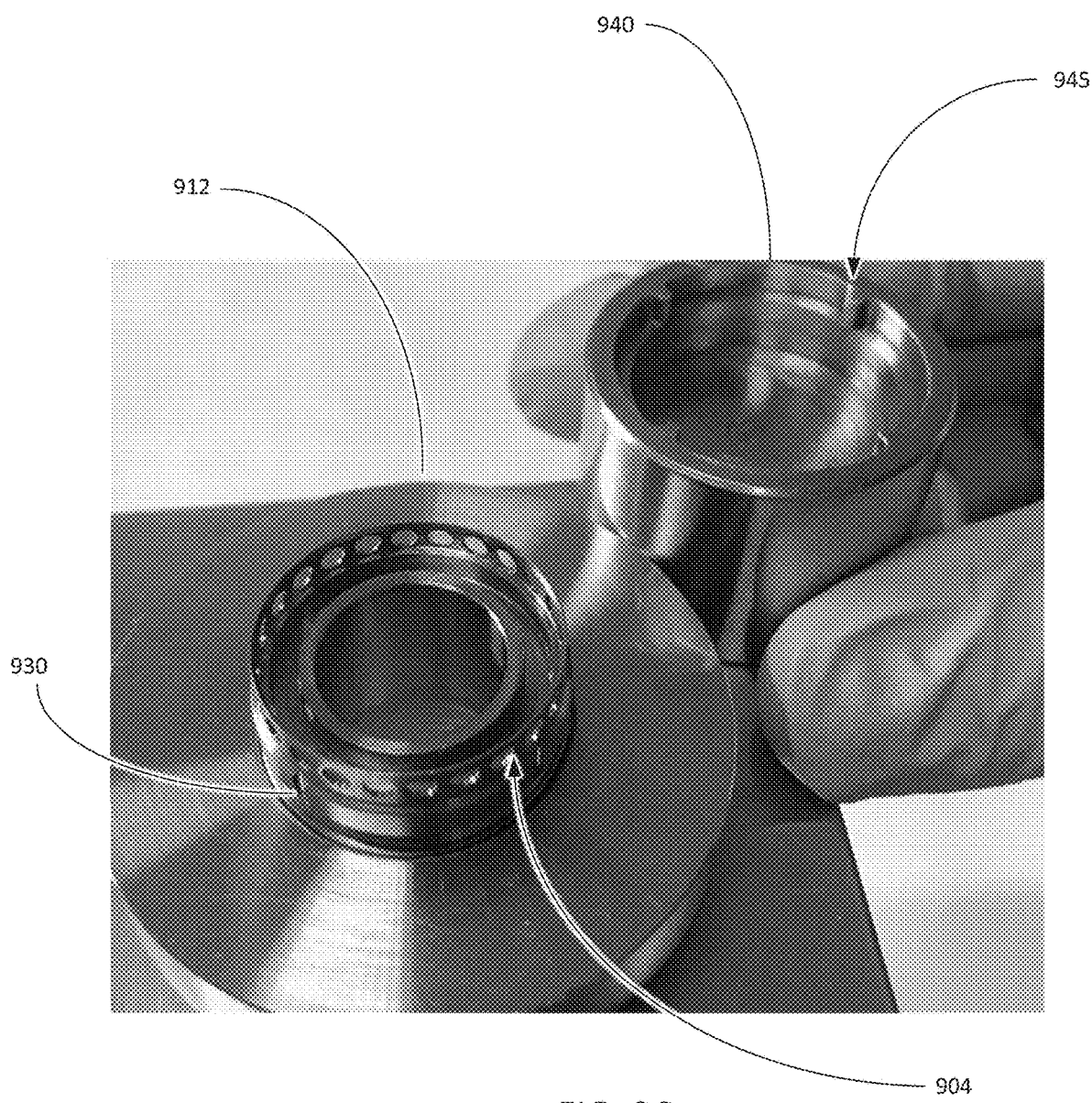

Referring now to FIGS. 9A-9C graft assembly 902 inserted in graft quick connect assembly 904, including collar 910 may be inserted into stationary receiver 912 and collar cover 900. Graft assembly 902, graft quick connect assembly 904, and collar 910 may be the same as or similar to graft assembly 702, graft quick connect assembly 704, and collar 710 of FIGS. 7A-7B. Also, stationary receiver 912 and collar cover 900 may be the same as or similar to stationary receiver 810 and collar cover 800 of FIG. 8.

As shown in FIG. 9B, graft assembly 902, graft quick connect assembly 904 and collar 910 may be positioned into the collar cover 900 until the threaded portion 907 of graft quick connect assembly 904 contacts and/or is aligned with threaded portion of collar cover 900 (e.g., threaded portion 820 of FIG. 8C). Referring now to FIG. 9C, graft quick connect assembly 904 may be positioned above stationary receiver 912, such that indentations 930 of graft quick connect assembly 904 are exposed and accessible. Socket 940 may be a cylindrical structure having an inner diameter that is larger than the outer diameter of graft quick connect assembly 904. Socket 940 may further include protrusions 945 which may extend inward from the inner diameter of socket 940 and may be designed to mate with or otherwise interface with indentations 930 of graft quick connect assembly 904 such that rotation of socket 940 causes rotation of graft quick connect assembly 904.

Figure 9D:
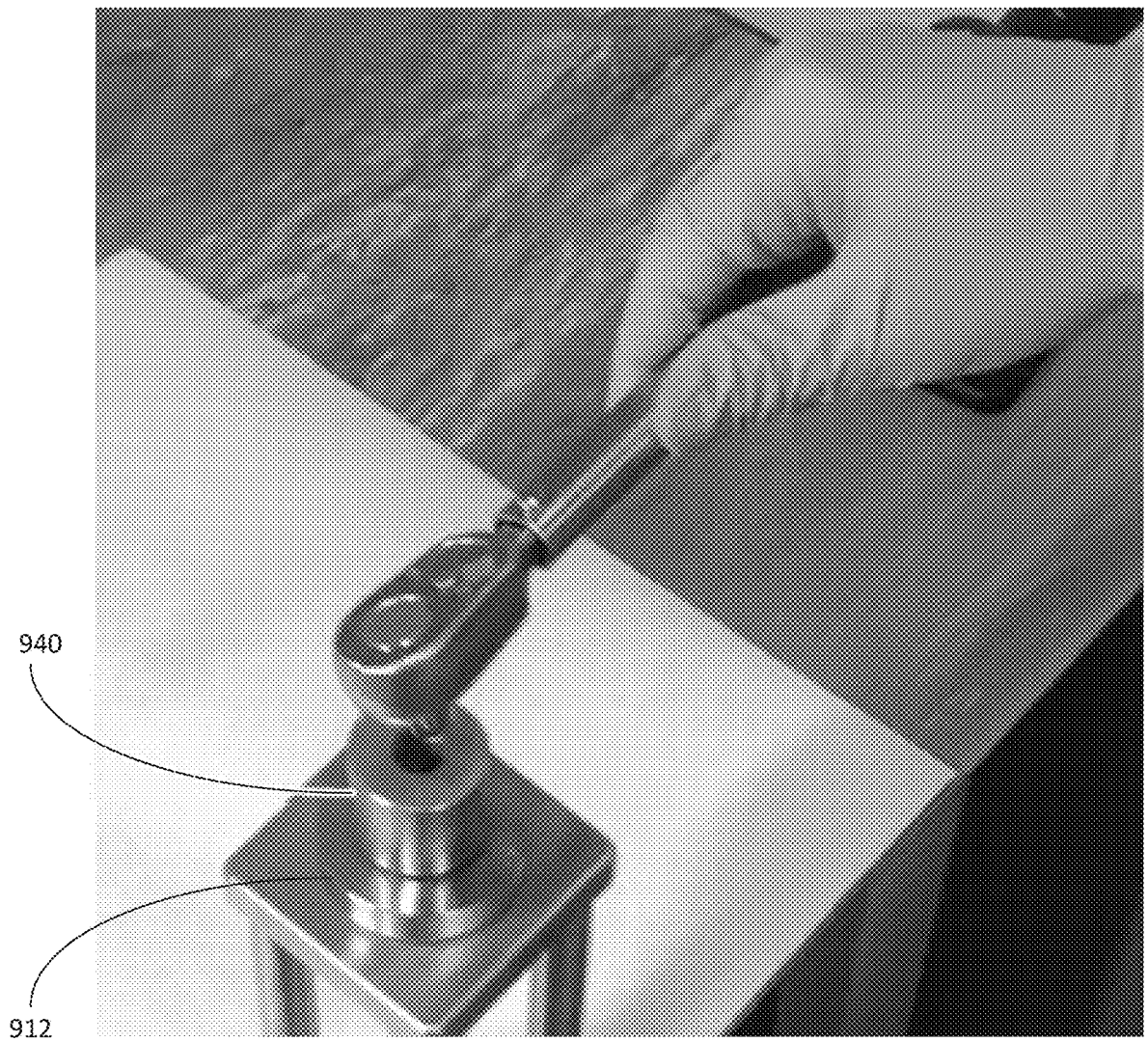

Referring now to FIG. 9D, socket 940 may include a receiver for mating with a wrench for turning socket 940 with respect to stationary receiver 912, As socket 940 is turned with respect to stationary receiver 912, the threads on the graft quick connect assembly (e.g., threaded portion 907 of FIG. 9B) are rotated with respect to the threads of the collar cover (e.g., threaded portion 820 of FIG. 8C) such that the graft quick connect assembly is secured to the collar cover.

Figure 10:
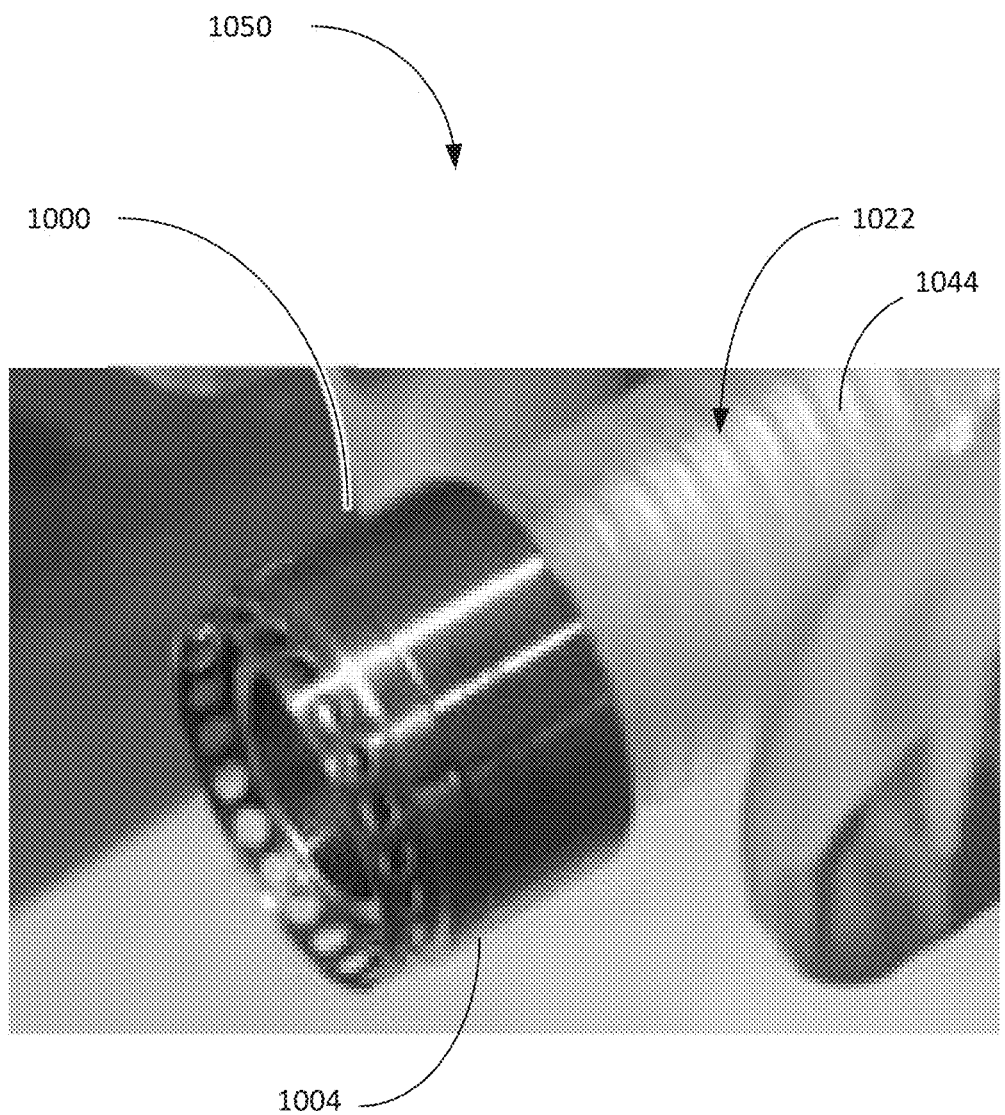
FIG. 10 illustrates a perspective view of a graft connect assembly, a collar cover, a graft tube, and a support tube.

Referring now to FIG. 10, graft connect assembly 1050 may be removed from the stationary receiver after applying the wrench to the socket connect the threads of graft quick connect assembly 1004 to the threads of collar cover 1000. As shown in FIG. 10, graft connect assembly 1050 may include graft quick connect assembly 1004, collar cover 1000, graft tube 1022 and support tube 1044. Graft tube 1022 and support tube 1044 may be the same or similar to graft tube 602 and support tube 604 of FIG. 6.

Referring now to FIGS. 11A-11D, graft connect assembly 1200 and pump assembly 1201 are depicted. Graft connect assembly 1200 may be the same as graft connect assembly 1050 of FIG. 10. For example, graft connect assembly 1200 may form a cylindrical structure may include graft tube 1204 and support tube 1202, which may be the same as graft tube 602 and support tube 604 of FIG. 6. Graft tube 1204 may be connected to support tube 1202 (e.g., via sutures). Support tube 1202 may include connection section 1206, which may be the same as connector section 624 of FIG. 6. Connection section 1206 may connect to graft quick connect assembly 1208, which may be the same as graft quick connect assembly 610 of FIG. 6.

Figure 11A:
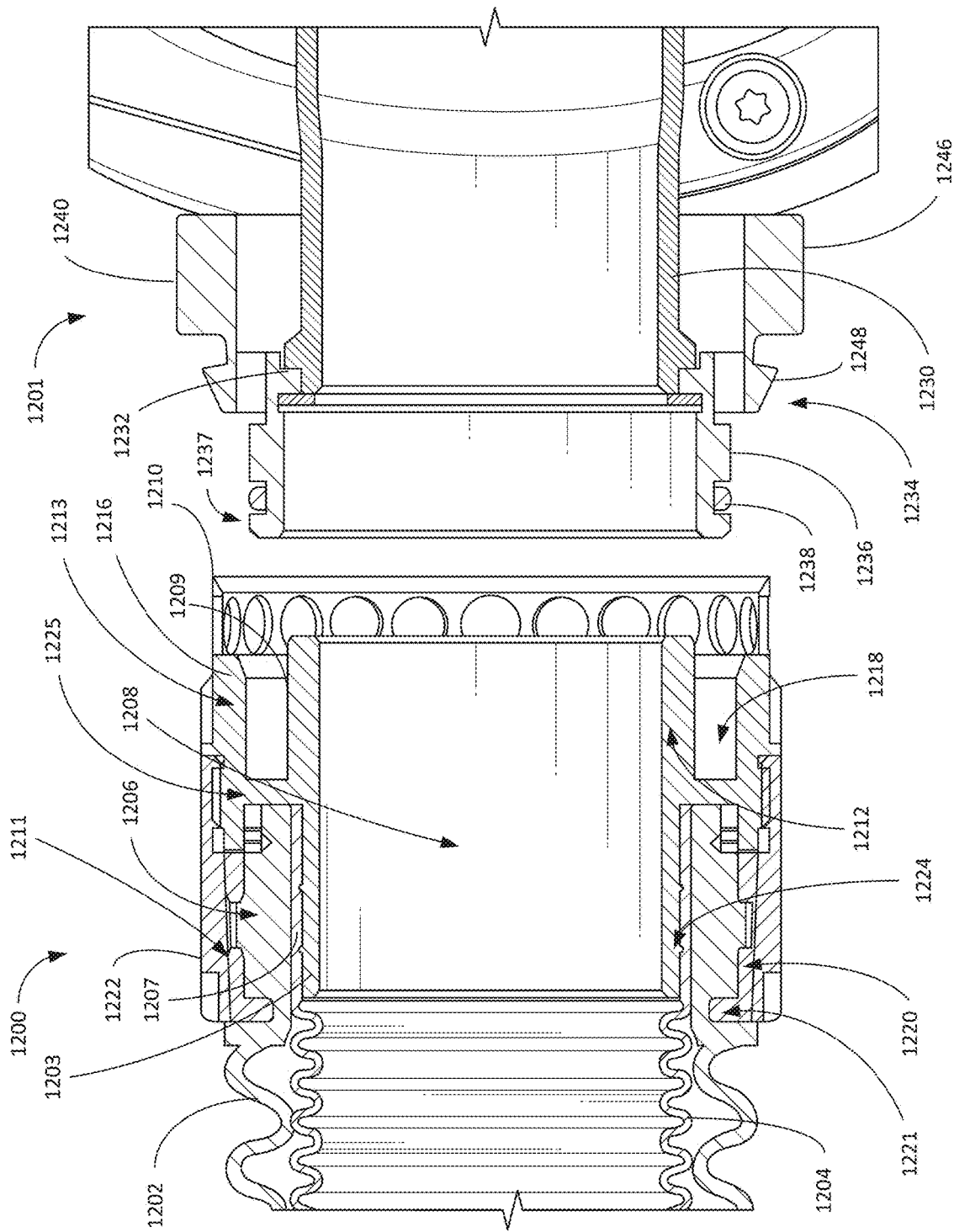
FIGS. 11A-11D illustrate side and cross-sectional views of a graft connect assembly and a pump assembly.

As shown in FIG. 11A, graft quick connect assembly 1200 may include internal housing 1203 including outer surface 1207 and outer surface 1209. Internal housing 1203 may form internal flange 1224 which may extend into an internal diameter of graft tube 1204. Internal flange 1224 may be include circumferential protrusions to enhance connection to graft tube 1204. An end of graft tube 1204 (e.g., connection section 1206) may be positioned in a graft receiving area defined between inner surface 1211 and outer surface 1207. In one example, graft tube 1204 may optionally be adhered (e.g., glued) to internal flange 1224. Internal flange may transition into receiving flange 1212, which may have the same inner diameter as internal flange 1224 but may have a different outer diameter. The inner diameter of flange 1224 may be a blood-contacting portion of graft quick connect assembly 1208. Similarly, the inner diameter of pump outlet 1230 may be the blood-contacting portion of the pump outlet. It is understood that pump outlet 1230 may alternatively be the pump inlet and/or any other cannula of a heart pump or blood pump. As such the luminal surfaces may include a textured surface designed to retain adherent thrombus or a highly polished surface to prevent thrombus formation. The polished surfaces may be further enhanced through the application of a thromboresistant coating, such as diamond-like carbon (DLC), titanium nitride (TiN), or 2-methacryloyloxyethyl phosphorylcholine-based (MPC) surface treatments. Graft quick connect assembly 1208 may further include outer flange 1216 which may have an inner diameter larger than an outer diameter of receiving flange 1212. Receiving flange 1212 together with outer flange 1216 may define receiving channel 1218. Receiving flange 1212 may extend into or otherwise may be connected to connector flange 1210, which may include several holes extending therethrough.

Collar 1220 may be positioned over connection section 1206 and may be two separate pieces. Collar 1220 may be the same or similar to collar 710 of FIG. 7. Collar 1220 may include flange 1221 that may be the same as flange 712 and may be positioned into a recessed portion of support tube 1202 immediately before connection section 1206. Collar cover 1222 may be an external housing of graft quick connect assembly 1200 and may be positioned over collar 1220 and may be the same as collar cover 1000 of FIG. 10. The external housing may include inner surface 1211 and outer surface 1213. As shown in FIG. 11A, collar cover 1222 may be threadably connected to graft quick connect assembly 1208 and threaded connection 1225.

Pump assembly 1201 may include pump outlet, which may direct blood out of the pump and towards graft tube 1204. Pump outlet may be cylindrical in shape and may be metallic (e.g. titanium, stainless steel, alloy, etc.). It is understood that pump outlet may be any type of biocompatible material. Pump outlet 1230 may include recessed portion 1232 which may extend circumferentially about the end of pump outlet 1230. Connector assembly 1234 may be connected to pump outlet 1230. Connector assembly may include inner assembly 1236 which may be cylindrical in shape (e.g., a cylindrical protrusion) and may include a protrusion that may be received by recessed portion 1232 and may secure inner assembly 1236 to pump outlet 1230. Alternatively, or additionally, inner assembly 1236 may be welded, adhered, or otherwise connected to pump outlet 1230. Inner assembly 1236 (e.g., including the cylindrical protrusion) may be received by a pump receiving area between inner surface 1213 and outer surface 1209.

Inner assembly 1236 may include an inner diameter and an outer diameter that are sized to extend into and be received by receiving channel 1218. Inner assembly 1236 may further include a recessed portion 1237 that may be a circumferential recessed region for receiving a portion of sealing ring 1238. Sealing ring 1238 and receiving channel 1218 may form a fluid tight seal with outer surface 1213 to form a fluid tight seal between graft quick connect assembly 1200 and pump assembly 1201. Sealing ring 1238 may be any well-known sealing ring or O-ring.

Outer assembly 1240 may be positioned around outlet and may form one or more tabs. For example, outer assembly 1240 may be cylindrical in shape and/or may have a split in the cylindrical shape to facilitate formation of outer assembly 1240. A space may be defined between an inner diameter of outer assembly 1240 and an outer diameter of outlet 1230. Outer assembly 1240 may be connected only at the left side of outer assembly 1240 to inner assembly 1236. For example, outer assembly 1240 may be metallic and may be welded at its left side to inner assembly 1236. The right side of outer assembly 1240 may be freestanding and may be compressible to decrease a diameter of right side of outer assembly 1240. Outer assembly 1240 may include tabs 1246 for compressing the right side of outer assembly 1240. Outer assembly 1240 may further include circular protrusions 1248 that may be connected to and/or extend from tabs 1246 and may be caused to move inward towards outlet 1230 when tabs 1246 are compressed into a compressed state. As tabs 1246 are transitioned from an expanded position or state to a contracted position or state (e.g., via pinching), circular protrusions 1248 may be caused to move closer to one another. Circular protrusions 1248 may be angled such that the left side has a smaller diameter than the right side. For example, the left side may have a height that is lower than a height of the right side. It is understood that circular protrusions 1248 may have a circular profile or may be protrusions that are any other shape or design other than circular or cylindrical.

To connect outer assembly 1240 with connector flange 1210, tabs 1246 may be transitioned into a contracted state causing circular protrusions to move closer to one another and/or aligned with a through-hole of connector flange 1210. To extend circular protrusions through respective through-holes of connector flange 1210, tabs 1246 may be released and permitted to expand to an expanded state. As tabs 1246 transition to the expanded state, circular protrusions move apart and into through-holes of connector flange 1210, thereby locking pump assembly 1201 to graft connect assembly 1200. Once outer assembly 1240 is connected with connector flange 1210, pump assembly 1201 may be in fluid communication with graft connect assembly 1200.

Figure 11B:
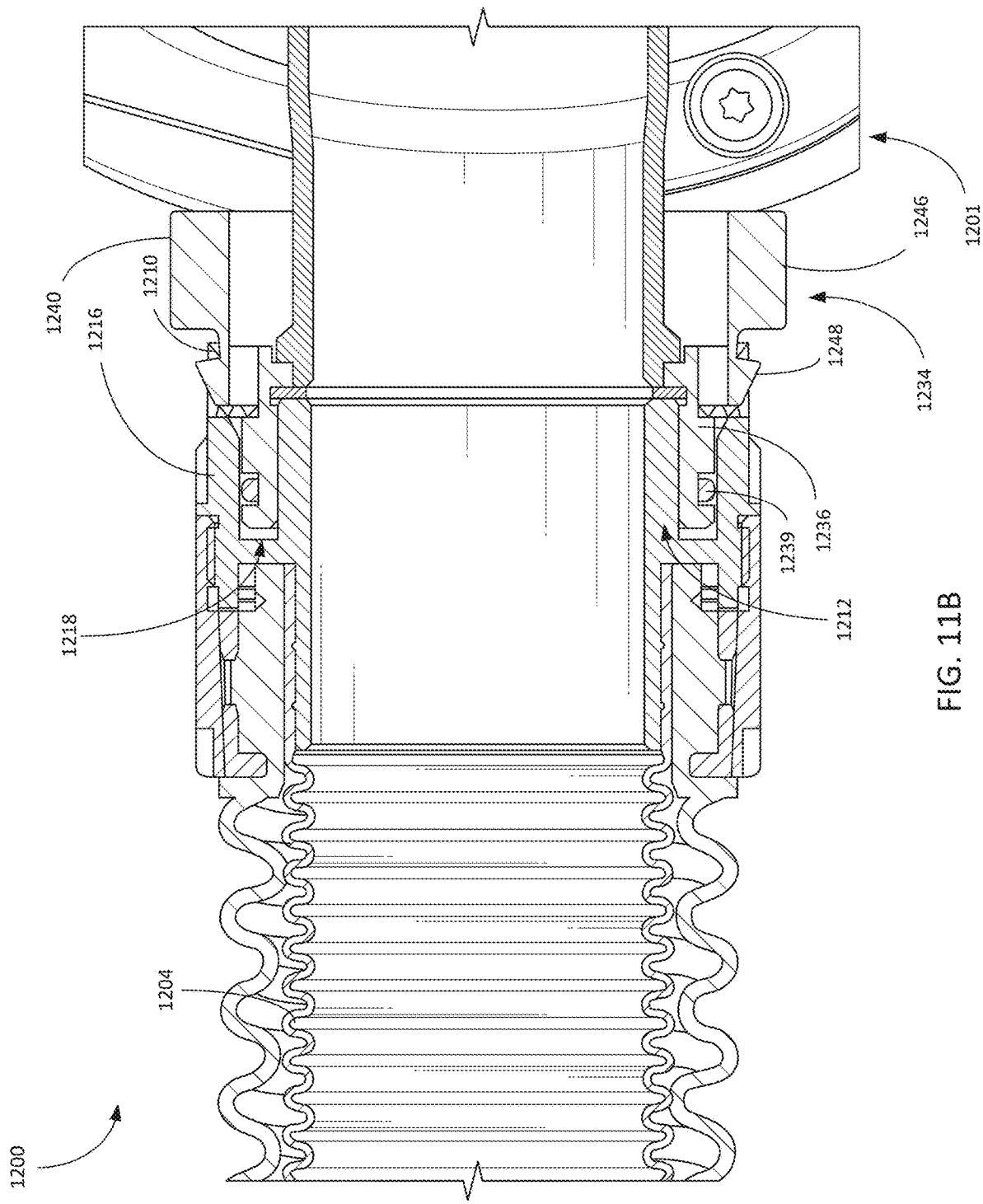

Referring now to FIG. 11B, graft connect assembly 1200 and pump assembly 1201 may be mated such that blood may flow therebetween. For example, inner assembly 1236 including sealing ring 1239 may inserted into and received by receiving channel 1218 defined by receiving flange 1212 together with outer flange 1216. Sealing ring may engage both graft connect assembly 1200 and pump assembly 1201 to form a fluid tight seal. Further circular protrusions, which may be angled, may be positioned into a corresponding through-hole of connector flange 1210. Flange 1210 may include through-holes arranged circumferentially. Circular protrusions may be sized to fit within the through-holes of flange 1210 and extend through the through-holes of flange 1210 to lock, connect, or otherwise secure graft quick connect assembly 1200 to pump assembly 1201. Outer assembly 1240 may transition from an expanded position or state to a contracted position or state to unlock and otherwise disconnect graft quick connect assembly 1200 and pump assembly 1201.

It may be desirable to release circular protrusions 1248 from connector flange 1210 to rotate graft tube 1204 with respect to pump assembly 1201. However, as blood may be flowing through graft connect assembly 1200, it is undesirable disengage graft connect assembly 1200 and pump assembly 1201. Instead, graft connect assembly 1200 may be rotated with respect pump assembly 1201 without disengaging graft connect assembly 1200 and pump assembly 1201 by compressing tabs 1246 to cause circular protrusions to exit corresponding through-holes of connector flange 1210. While tabs 1246 are compressed, graft connect assembly may be rotated with respect to pump assembly 1201 while sealing ring 1239 maintains a seal between receiving flange 1212 and inner assembly 1236. Once the desired position of graft connect assembly 1200 is achieved, tabs 1246 may be released and circular protrusions may engage a corresponding through-hole of connector flange 1210 to lock graft connect assembly 1200 to pump assembly 1201 to resist any axial or rotational movement between graft connect assembly 1200 and pump assembly 1201.

Figure 11C:
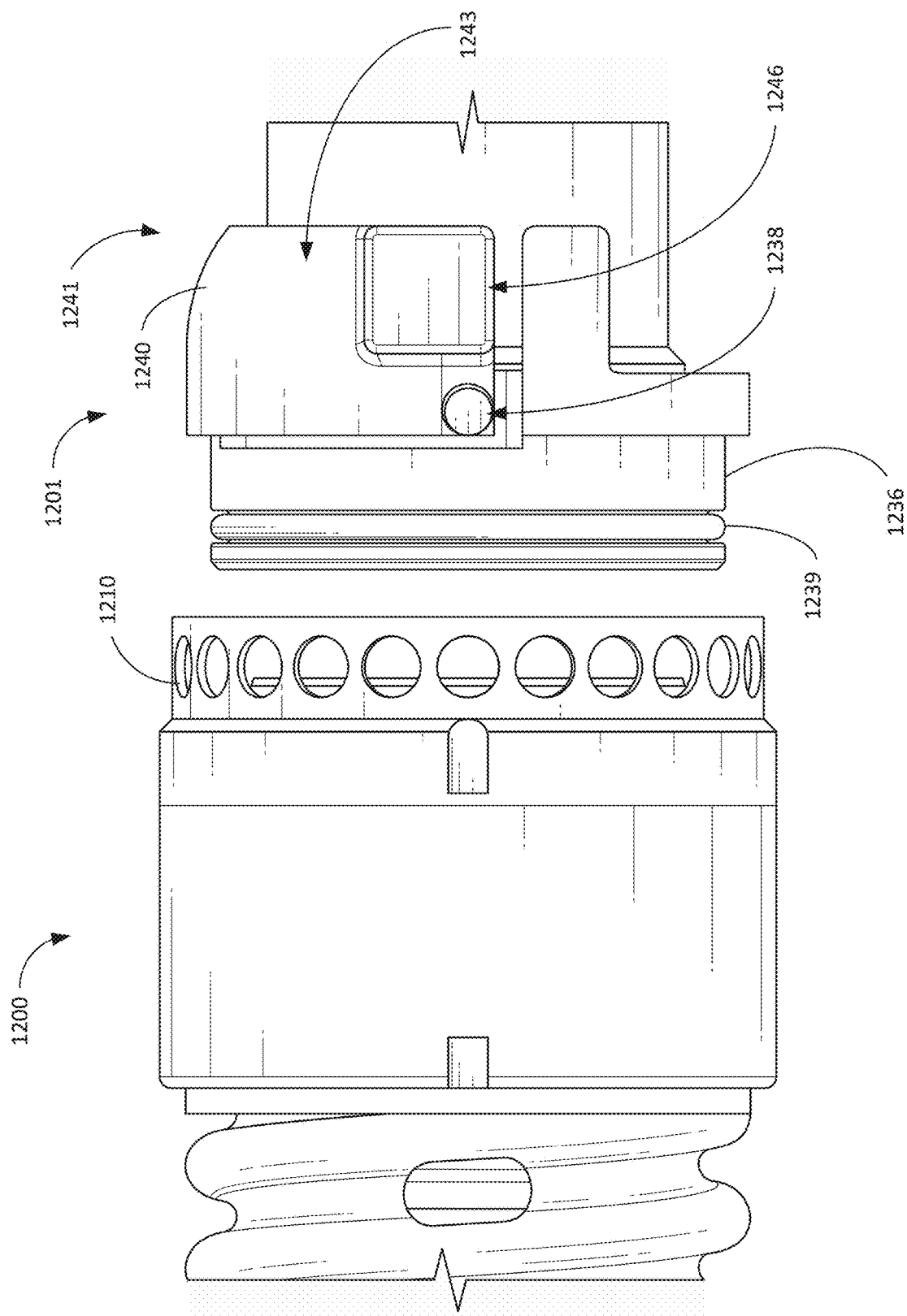
Figure 11D:
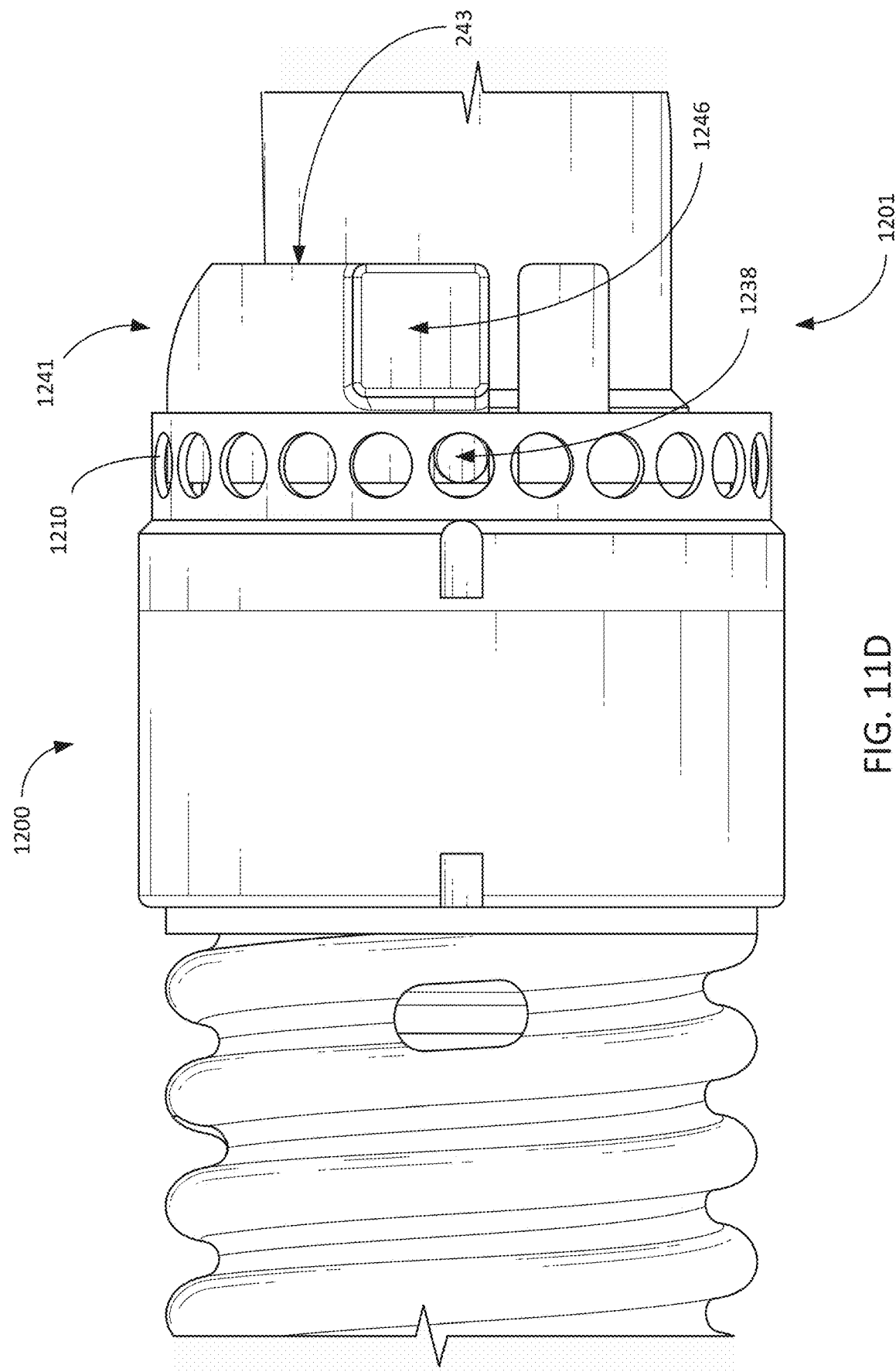

Referring now to FIG. 11C-11D, a perspective view of graft connect assembly 1200 and pump assembly 1201 are depicted. As shown in FIG. 11C, connector flange 1210 may extend circumferentially and include several through-holes. Further, sealing ring 1239 may be positioned near a left most region of inner assembly 1236. Circular protrusions 1236 may be an angled circular protrusion. Further tab 1246 may, in one example, be square in shape. It is understood that outer assembly 1240 may include reduced portions 1241 that may be a section of outer assembly 1240 having reduced length as compared to winged portion 1243 of outer assembly 1240 having tabs 1246. It is understood that winged portion 1243 may have greater flexibility and/or may be deformed a greater amount than reduced portions 1241.

Figure 12B:
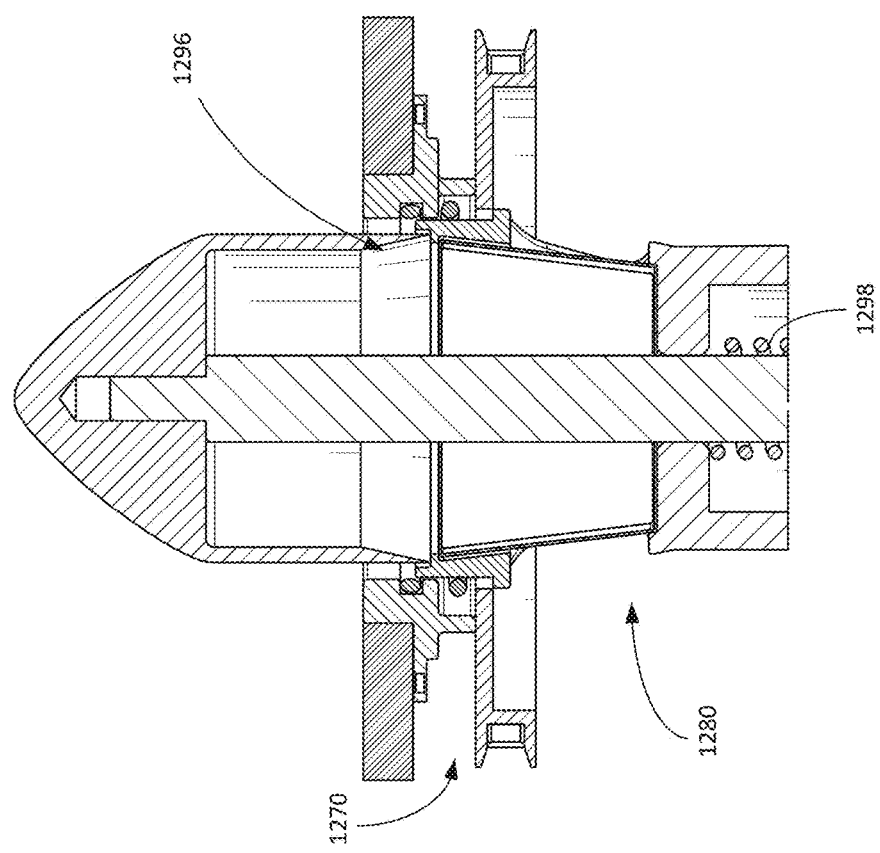
FIGS. 12A-12B illustrate perspective and cross-sectional views of a coring tool and an apical assembly.
Figure 12A:
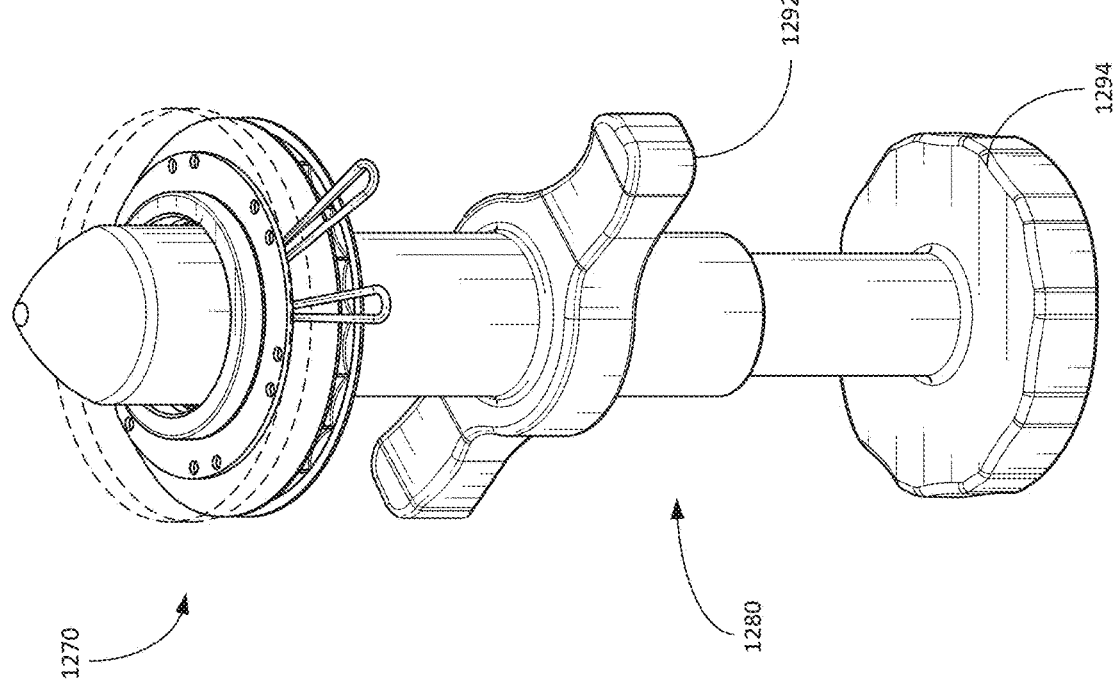

Referring now to FIGS. 12A-12B, coring tool may be used to cut a hole into the patient's heart suitable for pump installation. For example, coring tool 1280 may be sized to accommodate and connect to apical assembly 1270. It is understood that apical assembly 1270 may be any apical assembly described herein (e.g., apical assembly 1270). Coring took may include cutting portion 1296 for making a circular cut into the heart tissue (e.g., at the apex of the heart). Cutting portion 1296 may create hole having a diameter sized to receive the inlet of the pump. In one example, cutting portion 1296 may cut hole that is approximately 90% of the diameter of the inlet of the pump. This slight reduction in the size of the ventriculotomy compared to the pump inlet diameter ensures that the heart tissue applies a compression force to the pump inlet to help prevent blood from leaking from the heart chamber between the interface of the pump inlet and the heart tissue. The external portion of the cutting anvil wall includes at least one portion that is transparent to permit visualization that the core of tissue has been completed incised and captured by the cutting apparatus, before removing the coring tool from its position within the apical assembly 1270. Incomplete coring, in which a complete circular core of tissue, containing the full depth of the heart wall is not obtained, can lead to pump inlet malposition, thrombus within the heart chamber, and other deleterious effects. Removal of the coring tool from the apical assembly 1270 results in substantial bleeding when pump implantation is conducted without the use of cardiopulmonary bypass. Inspection of the cut tissue with the coring tool retained in position with the sewing ring permits confirmation of a suitable coring procedure or permits the tissue to be re-cored (i.e. the ventriculotomy repeated) to achieve a complete, circular, full heart wall depth incision to assist in optimal positioning of the pump in relation to the patient heart.

The surgeon may make a cruciate incision into the heart wall through the center of the sewing ring, then insert coring tool 1270 into the incision, until the extended diameter portion of the anvil engages with the sewing ring. It is understood that cutting portion may be attached to spring 1298 (e.g., to bias cutting portion into a closed position). Coring tool 1280 may further include hand grip 1292 to facilitate user control and grip and also may include knob 1294 which may be connected to cutting portion 1296 and/or may be in mechanical communication with spring 1298. The user may squeeze hand grip 1292 towards knob 1294, compressing spring 1298 and extending the cutting apparatus into the heart chamber. The tip of the cutting apparatus may be rounded to prevent damage to internal structures of the heart chamber, particularly chordae tendineae. The cutting edge of the blade may be oriented towards the endocardial surface of the heart wall similarly to prevent accidental incision of internal heart structures. After fully inserting the cutting apparatus, the user may release the compressive force on spring 1298 and rotate knob 1294 to turn cutting portion 1296 to completely incise the tissue captured by the cutting apparatus, as the cutting apparatus is retracted by spring 1298. Rotation or actuation of the cutting blade may be required to fully incise the 0.5-1.5 cm thick heart wall, for example.

Figure 13C:
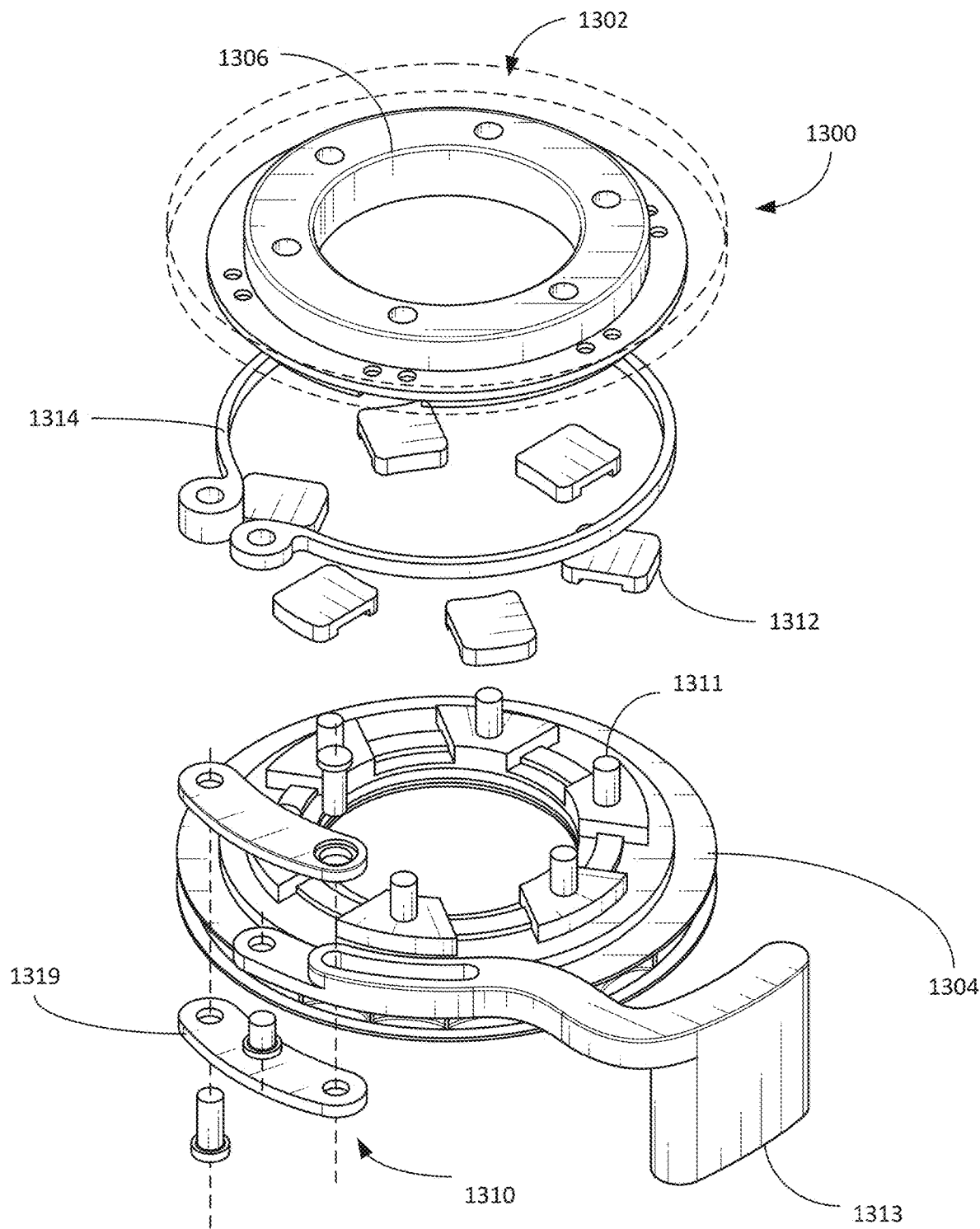
Figure 14A:
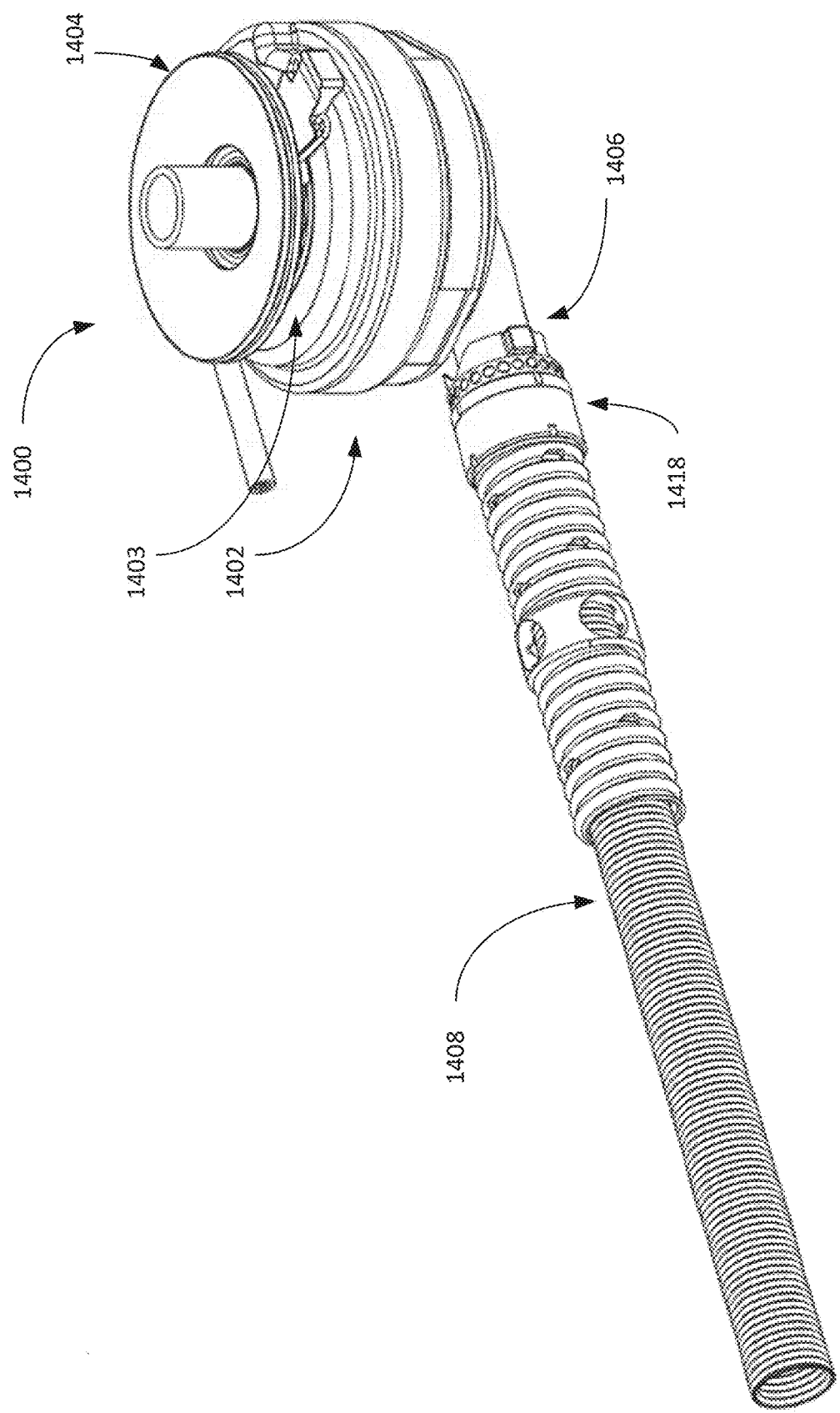
FIGS. 14A-14D illustrate perspective views of a heart pump system including a heart pump, an apical connector, a sewing ring, a pump quick connector, a graft connect assembly, and a graft quick connector.
Figure 14B:
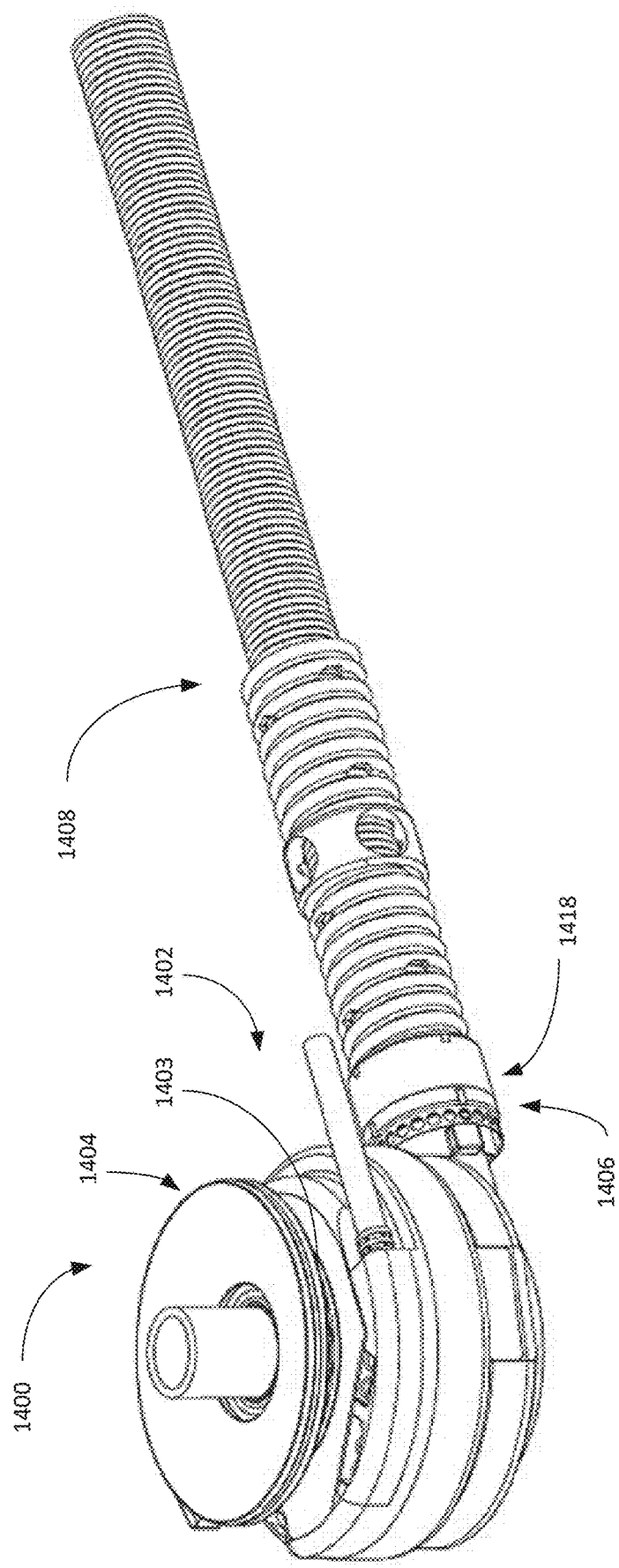
Figure 14C:
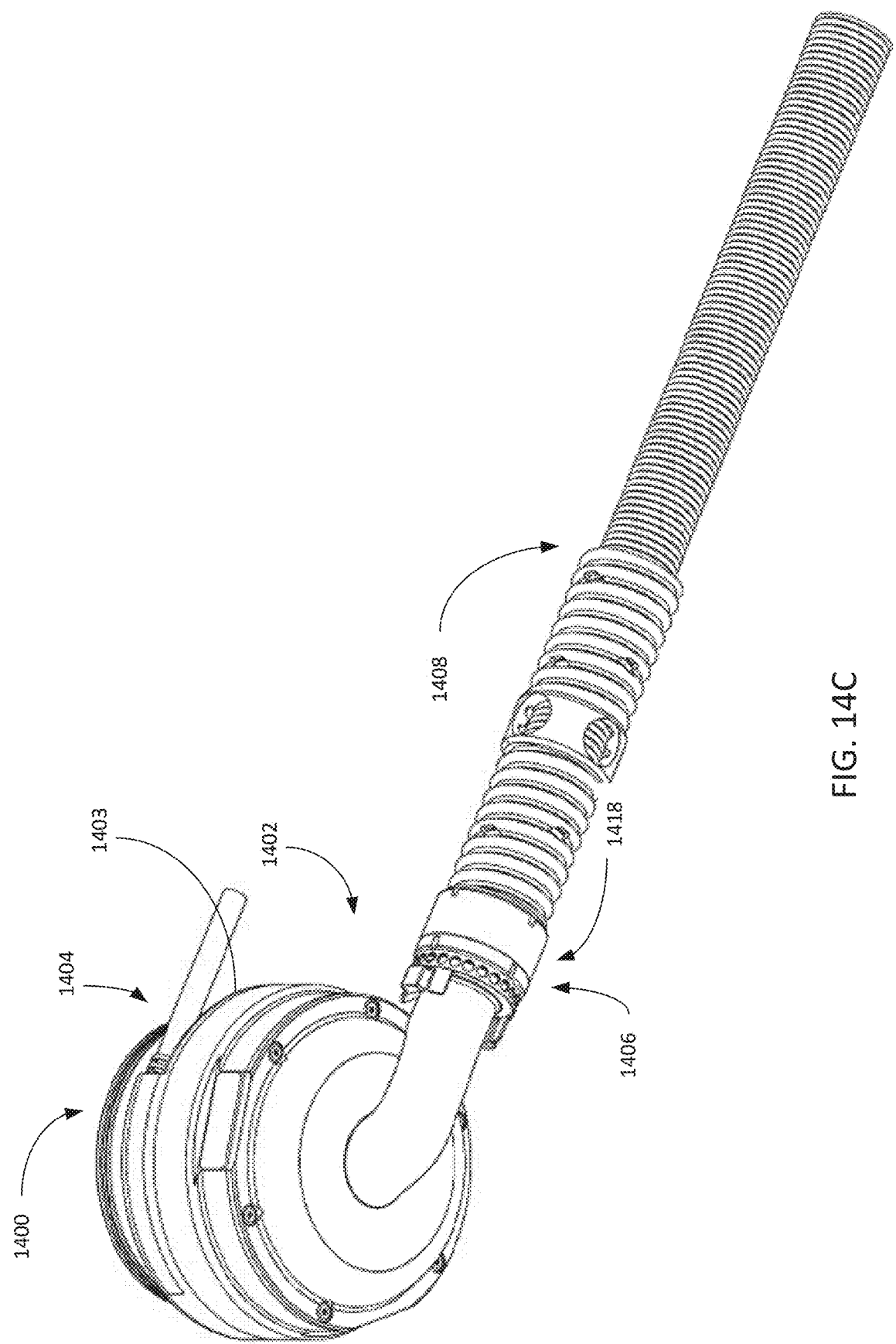
Figure 14D:
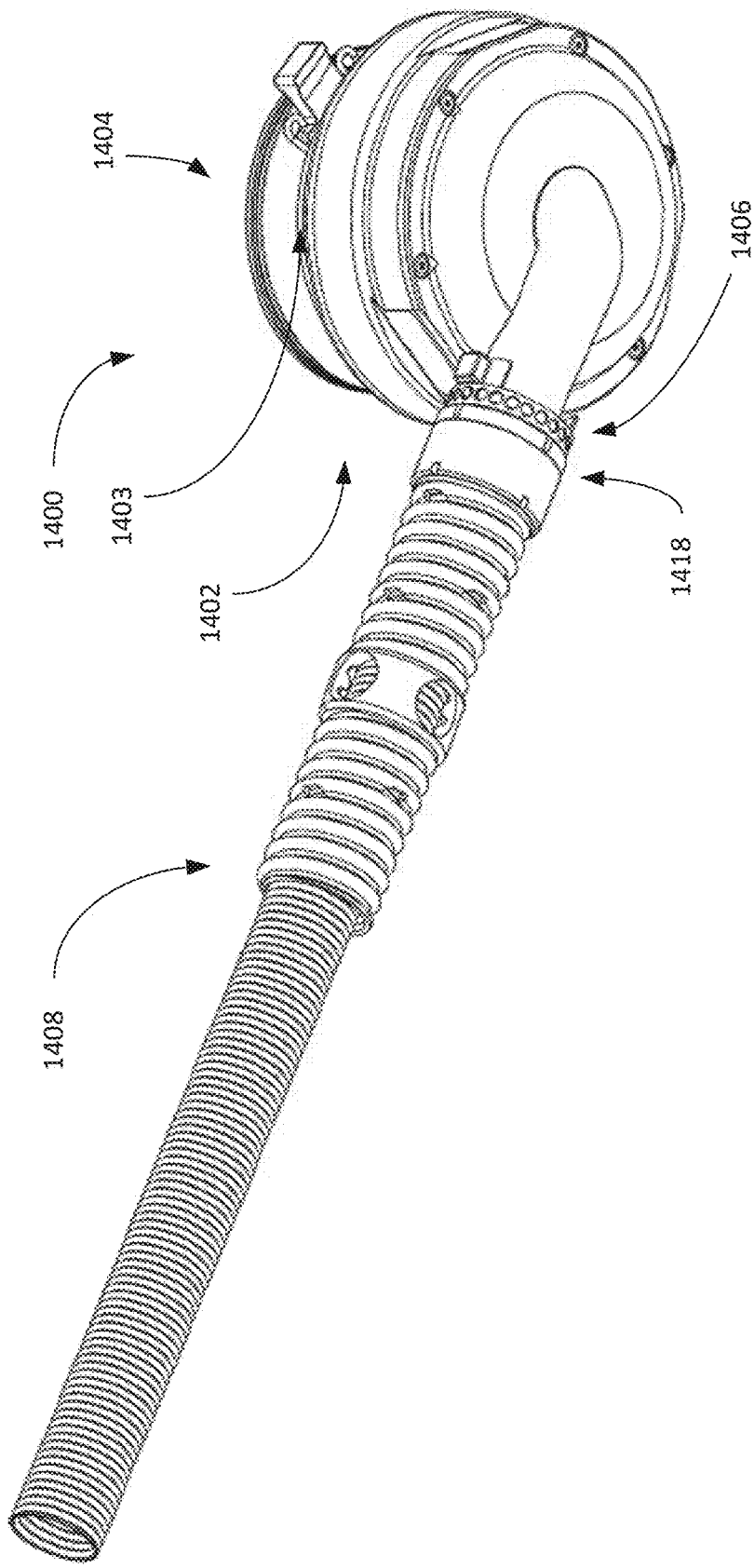

Referring to FIGS. 13A-13C, apical assembly 1300 is illustrated which may include a sewing ring 1302 that may be the same as or similar to sewing ring 204 of FIG. 2A. Sewing ring 1302 may be connected to ring support 1306 which may be an upper support and may be connected to connector housing 1304, which may be a lower support. Ring support 1306 may include an inner surface 1309 and a lower surface below and orthogonal to inner surface 1309.

Connector housing 1304 may include an inner surface 1307 and an upper surface above and orthogonal to inner surface 1307. Inner surface 1307 may include a recessed area in which sealing ring 1317 may be positioned for making a fluid tight seal with a portion of the heart pump extending into a channel or central aperture formed by inner surface 1309 and inner surface 1307. Connector housing may further include dimples similar to dimples 240 of FIG. 2A. Connector housing 1304 and ring support 1306 may be similar to connector housing 210 and ring support 212 of FIG. 2A. Ring support 1306 may include tightening assembly 1310 which may include a tab that may be opened and closed to tighten and loosen apical assembly 1300 with respect to the inlet of the pump.

Referring now to FIG. 13C, tightening assembly 1310, which may be a lock assembly, may include posts 1311 that each include and extend from a tapered base within ring support 1306 that permit locks 1312 to slide inward and outward guided by each tapered base which may form channels along which locks 1312 may move toward the inner surface of connector housing 1304. Locks may be restrained from movement in all other directions by each tapered base, an upper surface of connector housing and a lower surface of ring support 1306. Locks 1312 may be guided inward by tightening ring 1314, which may be caused to tighten or loosen by tab 1313 which may move between an open position and a closed position. In the closed position, tab 1313, which may be a handle, may tighten ring 1311 to cause locks 1312 to move inward and tighten against the inlet of the pump to secure apical assembly 1300 to the pump inlet via friction.

Tab 1313 may connect to one end of tightening ring and may include a slide extending through a portion of tab 1313. Arm 1319 may connect at one end of arm 1319 to a second end of tightening ring 1314 and may slidably connect to the slot of tab 1313 at a second end of arm 1319. In this manner, tab 1313 may be used to move the ends of tightening ring 1314 further apart and closer together. As tightening ring moves to a closed position with the two ends of tightening ring close to one another, locks 1312 may be caused to move in the channels towards the inner surface of connector housing 1304, ultimately extending partially beyond the inner surface. In the closed position, tightening ring 1314 may cause locks 1312 to contact a cannula or other structure of the heart pump to secure apical assembly 1300 to the heart pump.

Referring now to FIG. 14A-D, an exemplary implantable heart pump system is illustrated. As shown in FIGS. 14A-D, implantable heart pump system 1400 may include heart pump 1402, apical connector 1403, sewing ring 1404, pump quick connector 1406, graft connect assembly 1408, and graft quick connector 1418. Heart pump system 1400 may be the same or similar to heart pump system 100 of FIG. 1. Heart pump 1402, apical connector 1403, sewing ring 1404, pump quick connector 1406, graft connect assembly 1408, and graft quick connector 1418 may be the same or similar to heart pump 102, apical connector 103, sewing ring 104, pump quick connector 106, graft connect assembly 108, and graft quick connector 118 of FIG. 1.

The foregoing description of illustrative embodiments has been presented for purposes of illustration and of description. It will of course be understood that the embodiments described herein are illustrative, and components may be arranged, substituted, combined, and designed in a wide variety of different configurations, all of which are contemplated and fall within the scope of this disclosure. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An assembly for connecting a graft tube to a blood pump, the assembly comprising:
    a graft assembly configured to be coupled to an end of the graft tube, the graft assembly forming a cylindrical structure comprising:
        an internal housing having an first outer surface and a second outer surface;
        an external housing offset from the internal housing and defining a graft receiving area between a first inner surface of the external housing and the first outer surface of the internal housing and defining a pump receiving area between a second inner surface of external housing and the second outer surface of the internal housing;
        a flange extending from the cylindrical structure and having a plurality of through-holes arranged circumferentially;
    a pump assembly configured to be coupled to a cannula of the blood pump, the pump assembly comprising:
        a cylindrical protrusion sized and configured to be received in the pump receiving area; and
        a set of protrusions extending from the cylindrical protrusion and configured to be received by and extend through a set of through-holes of the plurality of through-holes of the flange.

2. The assembly of claim 1, wherein the cannula is an outlet of the blood pump and wherein the cylindrical protrusion is configured to rotatably couple to the outlet of the blood pump such that the pump assembly is free to rotate with respect to the outlet of the blood pump while the cylindrical protrusion is coupled the outlet of the blood pump.

3. The assembly of claim 1, wherein the cylindrical protrusion comprises a sealing ring configured to create fluid-tight seal between the graft assembly and the pump assembly.

4. The assembly of claim 3, wherein the pump assembly is configured to rotate with respect to the graft assembly while the cylindrical protrusion is received in the pump receiving area and the sealing ring maintains a fluid-tight seal.

5. The assembly of claim 1, wherein the pump assembly further comprises a set of tabs extending from the set of protrusions, the set of tabs configured to be depressed to transition the set protrusions between an expanded position and a contracted position.

6. The assembly of claim 5, wherein the set of protrusions are configured to move closer together when the set of tabs are in the contracted position and are configured to move further apart when the set of tabs are in the expanded position.

7. The assembly of claim 1, wherein the set of protrusions are configured to lock the pump assembly to the graft assembly when the set of protrusions extend through the set of through-holes of the flange.

8. The assembly of claim 1, wherein the each protrusion of the set of protrusions has a first end having a first height and a second end having a second height higher than the first height.

9. The assembly of claim 1, wherein the each protrusion of the set of protrusions has a circular profile.

10. The assembly of claim 1, wherein the graft receiving area is configured to receive and couple to the end of the graft tube to secure the graft assembly to the graft tube.

11. A method for connecting a graft tube to a heart pump via an assembly comprising a graft assembly and a pump assembly, the method comprising:
    positioning the graft assembly adjacent to the pump assembly, the graft assembly configured to be coupled to an end of a graft tube and comprising a cylindrical structure and a flange extending from the cylindrical structure and having a plurality of through-holes, the pump assembly comprising a cylindrical protrusion configured to be to be coupled to a cannula of the heart pump;
    causing a set of tabs on the pump assembly to transition to a compressed state, the set of tabs each having a protrusion and each extending from the cylindrical protrusion of the pump assembly;
    aligning the protrusions of each of the tabs with the through-holes of the flange of the graft assembly while the tabs are in the compressed state;
    causing the protrusions of each of the tabs to extend through respective through-holes of the plurality of through-holes of the flange by transitioning the set of tabs to an expanded state while the protrusions of each of the tabs are aligned with the through-holes of the flange,
    wherein the cylindrical protrusion engages and is in fluid communication with the cylindrical structure when the protrusions of each of the tabs extend through the respective through-holes.

12. The method of claim 11, wherein the cylindrical structure of the graft assembly comprises an internal housing and an external housing and a pump receiving area is defined between the internal housing and the external housing.

13. The method of claim 12, wherein a portion of the cylindrical protrusion is received by the pump receiving area when the protrusions of each of the tabs extends through respective through-holes of the plurality of through-holes of the flange.

14. The method of claim 12, wherein the cylindrical structure of the graft assembly and cylindrical protrusion of the pump assembly form a fluid tight seal between the graft tube and the cannula when the protrusions of each of the tabs extend through respective through-holes of the plurality of through-holes of the flange.

15. The method of claim 12, wherein the cylindrical protrusion has sealing ring and, when the cylindrical protrusion is received by the pump receiving area, the sealing ring engages both the cylindrical protrusion and the cylindrical structure.

16. The method of claim 12, wherein a graft receiving area is defined between the internal housing and the external housing and the graft receiving area is configured to receive the end of the graft tube.

17. The method of claim 11, wherein the plurality of through-holes of the flange are arranged circumferentially.

18. The method of claim 11, wherein the cylindrical protrusion and the cannula are coaxial along a first axis and the cylindrical protrusion is permitted to rotate along the first axis with respect to the cannula when the cylindrical protrusion is coupled to the cannula.

19. The method of claim 11, wherein each through-hole of the plurality of through-holes is circular in shape and the protrusions of each of the tabs has a circular profile.

20. The method of claim 11, wherein the protrusions of each of the tabs are positioned closer to one another when the set of tabs are in the compressed state than when each of the tabs are in the expanded state.

* * * * *